US012241089B2

(12) United States Patent
Kaneko et al.

(10) Patent No.: US 12,241,089 B2
(45) Date of Patent: Mar. 4, 2025

(54) METHOD FOR INDUCING T CELLS FOR CELL-BASED IMMUNOTHERAPY FROM PLURIPOTENT STEM CELLS

(71) Applicants: Kyoto University, Kyoto (JP); Thyas Co. Ltd., Kyoto (JP)

(72) Inventors: Shin Kaneko, Kyoto (JP); Hiroshi Kawamoto, Kyoto (JP); Kyoko Masuda, Kyoto (JP); Atsutaka Minagawa, Kyoto (JP); Akitsu Hotta, Kyoto (JP); Yutaka Shimazu, Kyoto (JP); Hiroshi Ichise, Kyoto (JP)

(73) Assignees: Kyoto University, Kyoto (JP); Thyas Co. Ltd., Kyoto (JP)

(*) Notice: Subject to any disclaimer, the term of this patent is extended or adjusted under 35 U.S.C. 154(b) by 370 days.

(21) Appl. No.: 15/326,977

(22) PCT Filed: Jul. 17, 2015

(86) PCT No.: PCT/JP2015/070608

§ 371 (c)(1),
(2) Date: Aug. 17, 2017

(87) PCT Pub. No.: WO2016/010148

PCT Pub. Date: Jan. 21, 2016

(65) Prior Publication Data

US 2017/0369850 A1 Dec. 28, 2017

Related U.S. Application Data

(60) Provisional application No. 62/026,341, filed on Jul. 18, 2014, provisional application No. 62/026,332, filed on Jul. 18, 2014.

(51) Int. Cl.

| | |
|---|---|
| ***C12N 5/074*** | (2010.01) |
| ***A61K 35/14*** | (2015.01) |
| ***A61K 35/17*** | (2015.01) |
| ***A61K 39/00*** | (2006.01) |
| ***A61P 35/00*** | (2006.01) |
| ***C12N 5/0783*** | (2010.01) |
| ***C12N 5/10*** | (2006.01) |

(52) U.S. Cl.

CPC ............ *C12N 5/0696* (2013.01); *A61K 35/14* (2013.01); *A61K 39/4611* (2023.05); *A61K 39/4632* (2023.05); *A61K 39/464453* (2023.05); *A61K 39/464838* (2023.05); *A61P 35/00* (2018.01); *C12N 5/0636* (2013.01); *C12N 5/0638* (2013.01); *C12N 5/10* (2013.01); *C12N 2501/515* (2013.01); *C12N 2506/45* (2013.01); *C12N 2510/00* (2013.01)

(58) Field of Classification Search

CPC ......... C12N 5/0696; C12N 5/10; A61K 35/17
See application file for complete search history.

(56) References Cited

U.S. PATENT DOCUMENTS

| | | | |
|---|---|---|---|
| 8,048,999 B2 | 11/2011 | Yamanaka et al. | |
| 8,278,104 B2 | 10/2012 | Yamanaka et al. | |
| 8,877,493 B2 | 11/2014 | Sekiguchi et al. | |
| 9,127,256 B2 | 9/2015 | Fusaki et al. | |
| 9,546,384 B2 * | 1/2017 | Frendewey .......... | C12N 15/907 |
| 9,683,232 B2 | 6/2017 | Yamanaka et al. | |
| 2008/0213885 A1 | 9/2008 | Tryggvason et al. | |
| 2011/0117645 A1 | 5/2011 | Yasuda | |
| 2013/0078226 A1 | 3/2013 | Nakauchi et al. | |

FOREIGN PATENT DOCUMENTS

| | | |
|---|---|---|
| EP | 2 853 590 A1 | 4/2015 |
| WO | WO2006/132524 A1 | 12/2006 |
| WO | WO2007/069666 A1 | 6/2007 |
| WO | WO2008/118820 A2 | 10/2008 |
| WO | WO2009/007852 A2 | 1/2009 |
| WO | WO2009/032194 A1 | 3/2009 |
| WO | WO2009/057831 A1 | 5/2009 |
| WO | WO2009/058413 A1 | 5/2009 |
| WO | WO2009/075119 A1 | 6/2009 |
| WO | WO2009/079007 A1 | 6/2009 |
| WO | WO2009/091659 A2 | 7/2009 |
| WO | WO2009/101084 A1 | 8/2009 |
| WO | WO2009/101407 A2 | 8/2009 |
| WO | WO2009/102983 A2 | 8/2009 |
| WO | WO2009/114949 A1 | 9/2009 |
| WO | WO2009/117439 A2 | 9/2009 |
| WO | WO2009/123349 A1 | 10/2009 |
| WO | WO2009/126250 A2 | 10/2009 |

(Continued)

OTHER PUBLICATIONS

Delmonte et al., Journal of Clinical Immunology (2018) 38:646-655. (Year: 2018).*
Nakatsuji et al., Nature Biotechnology, 26(7): 739-740, Jul. 2008). (Year: 2008).*
Vizcardo et al., Cell Stem Cell, 12:31-36, Jan. 3, 2013, supplemental materials, pp. 1-9.*
Fong et al., Molecular Immunology 37: 391-402, 2000.*
Eljaafari J Immunol ; 190:184-194 (Year: 2013).*
Yu et al The Journal of Experimental Medicine • vol. 197, No. 4, 475-487 (Year: 2003).*
Eminli et al. (2008) "Reprogramming of Neural Progenitor Cells into Induced Pluripotent Stem Cells in the Absence of Exogenous Sox2 Expression," Stem Cells, 26, pp. 2467-2474.

(Continued)

*Primary Examiner* — Anoop K Singh

(74) *Attorney, Agent, or Firm* — Gavrilovich, Dodd & Lindsey LLP

(57) ABSTRACT

Provided is a method for inducing T cells for a cell-based immunotherapy, comprising the steps of:

(1) providing Rag 1 and/or Rag 2 gene knockout human pluripotent stem cells bearing genes encoding a T cell receptor specific for a desired antigen, and (2) inducing T cells from the pluripotent stem cells of step (1). Further provided are a cell-based immunotherapy method that uses the T cells for the cell-based immunotherapy and an iPS cell bank for the cell-based immunotherapy.

4 Claims, 20 Drawing Sheets

Specification includes a Sequence Listing.

(56) References Cited

FOREIGN PATENT DOCUMENTS

| | | | |
|---|---|---|---|
| WO | WO2009/126251 | A2 | 10/2009 |
| WO | WO2009/126655 | A2 | 10/2009 |
| WO | WO2009/157593 | A1 | 12/2009 |
| WO | WO2010/008054 | A1 | 1/2010 |
| WO | WO2010/009015 | A2 | 1/2010 |
| WO | WO2010/013845 | A1 | 2/2010 |
| WO | WO2010/033906 | A2 | 3/2010 |
| WO | WO2010/033920 | A2 | 3/2010 |
| WO | WO2010/042800 | A1 | 4/2010 |
| WO | WO2010/050626 | A1 | 5/2010 |
| WO | WO2010/056831 | A2 | 5/2010 |
| WO | WO2010/068955 | A2 | 6/2010 |
| WO | WO2010/098419 | A1 | 9/2010 |
| WO | WO2010/102267 | A2 | 9/2010 |
| WO | WO2010/111409 | A2 | 9/2010 |
| WO | WO2010/111422 | A2 | 9/2010 |
| WO | WO2010/115050 | A2 | 10/2010 |
| WO | WO2010/124290 | A2 | 10/2010 |
| WO | WO2010/137746 | A1 | 12/2010 |
| WO | WO2010/147395 | A2 | 12/2010 |
| WO | WO2010/147612 | A1 | 12/2010 |
| WO | WO2011/043405 | A1 | 4/2011 |
| WO | WO2011/096482 | A1 | 8/2011 |
| WO | 2013/176197 | A1 | 11/2013 |
| WO | WO-2014165707 | A2 * | 10/2014 |
| WO | 2015/099134 | A1 | 7/2015 |

OTHER PUBLICATIONS

Feng et al. (2008) "Reprogramming of fibroblasts into induced pluripotent stem cells with orphan nuclear receptor Esrrb," Nat Cell Biol., 11, pp. 197-203.

Han et al. (2010) "Tbx3 improves the germ-line competency of induced pluripotent stem cells," Nature, 463, pp. 1096-1100.

Heng et al. (2009) "The Nuclear Receptor Nr5a2 Can Replace Oct4 in the Reprogramming of Murine Somatic Cells to Pluripotent Cells," Cell Stem Cell, 6, pp. 167-174.

Huangfu et al. (2008) "Induction of pluripotent stem cells from primary human fibroblasts with only Oct4 and Sox2," Nat. Biotechnol., 26, pp. 1269-1275.

Ichida et al. (2009) "A Small-Molecule Inhibitor of Tgf-b Signaling Replaces Sox2 in Reprogramming by Inducing Nanog" Cell Stem Cell, 5, pp. 491-503.

Yu et al. (2007) "Induced Pluripotent Stem Cell Lines Derived from Human Somatic Cells," Science, 318, pp. 1917-1920.

Takahashi et al. (2007) "Induction of Pluripotent Stem Cells from Adult Human Fibroblasts by Defined Factors," Cell, 131, pp. 861-872.

Kim et al. (2009) "Direct reprogramming of human neural stem cells by OCT4," Nature, 461, pp. 649-643.

Lyssiotis et al. (2009) "Reprogramming of murine fibroblasts to induced pluripotent stem cells with chemical complementation of Klf4," Proc. Natl. Acad. Sci., 106, pp. 8912-8917.

Mali et al. (2010) "Butyrate Greatly Enhances Derivation of Human Induced Pluripotent Stem Cells by Promoting Epigenetic Remodeling and the Expression of Pluripotency-Associated Genes," Stem Cells., 28, pp. 713-720.

Marson et al. (2008) "Wnt signaling promotes reprogramming of somatic cells to pluripotency," Cell Stem Cell., 3, pp. 132-135.

Nakagawa et al. (2008) "Generation of induced pluripotent stem cells without Myc from mouse and human fibroblasts," Nat. Biotechnol., 26, pp. 101-106.

Judson et al. (2009) "Embryonic stem cell specific microRNAs promote induced pluripotency," Nat. Biotech., 27, pp. 459-461.

Shi et al. (2008) "A Combined Chemical and Genetic Approach for the Generation of Induced Pluripotent Stem Cells," Cell Stem Cell., 2, pp. 525-5283.

Shi et al. (2008) "A Combined Chemical and Genetic Approach for the Generation of Induced Pluripotent Stem Cells," Cell Stem Cell., 3, pp. 568-574.

Zhao et al. (2008) "Two Supporting Factors Greatly Improve the Efficiency of Human iPSC Generation," Cell Stem Cell., 3, pp. 475-479.

Bendle et al. (2010) "Two Supporting Factors Greatly Improve the Efficiency of Human iPSC Generation," Nat. Med., 16(5), pp. 565-570.

Takahashi et al. (2006) "Induction of Pluripotent Stem Cells from Mouse Embryonic and Adult Fibroblast Cultures by Defined Factors," Cell, 126, pp. 663-676.

Cyranoski et al. (2012) "Stem-cell pioneer banks on future therapies," Nature, 488, 139, 2 pp.

Huangfu et al. (2008) "Induction of pluripotent stem cells by defined factors is greatly improved by small-molecule compounds," Nat. Biotechnol., 26, pp. 795-797.

Ito et al. (1988) "Change of HLA phenotype in postoperative erythroderma," Lancet, 331, p. 413.

Cong et al. (2013) "Multiplex Genome Engineering Using CRISPR/Cas Systems," Science, 39; 819, 9 pp.

Maekawa et al. (2011) "Direct reprogramming of somatic cells is promoted by maternal transcription factor Glis1," Nature, 474, 7 pp.

Morgan et al. (2006) "Cancer Regression in Patients After Transfer of Genetically Engineered Lymphocytes," Science, 314, 5 pp.

Nishimura et al. (2013) "Generation of Rejuvenated Antigen-Specific T Cells by Reprogramming to Pluripotency and Redifferentiation," Cell Stem Cell, pp. 114-126.

Mali et al. (2013) "RNA-Guided Human Genome Engineering via Cas9," Science, 39: 8 pp.

Okita et al. (2008) "Generation of Mouse Induced Pluripotent Stem Cells Without Viral Vectors," Science, 322, pp. 949-953.

Kaneko (2014), The Medical Frontline, 69, pp. 724-733.

Sun et al. (2009) "Feeder-free derivation of induced pluripotent stem cells from adult human adipose stem cells," Proc. Natl. Acad. Sci., 106, pp. 15720-15725.

Takahashi et al. (2009) "Human Induced Pluripotent Stem Cells on Autologous Feeders," PLoS One, 4, 6 pp.

Timmermans et al. (2009) "Generation of T Cells from Human Embryonic Stem Cell-Derived Hematopoietic Zones," Journal of Immunology, 182, pp. 6879-6888.

Vizcardo et al. (2013) "Regeneration of Human Tumor Antigen-Specific T Cells from iPSCs Derived from Mature CD8+ T Cells," Cell Stem Cell, 12, pp. 31-36.

Warren et al. (2010) "Highly Efficient Reprogramming to Pluripotency and Directed Differentiation of Human Cells with Synthetic Modified mRNA," Cell Stem Cell., 7, pp. 618-630.

Yoshida et al. (2009) "Hypoxia Enhances the Generation of Induced Pluripotent Stem Cells," Cell Stem Cell., 5, pp. 237-241.

Nakajima (2013), Hematology Frontier, vol. 23, No. 8, pp. 1105-1110.

Gattinoni et al. (2006) "Adoptive immunotherapy for cancer: building on success," The Journal of Immunology, vol. 6, No. 5, pp. 383-393.

Lei et al. (Jul. 2011) "In Vivo Programming of Tumor Antigen-Specific T Lymphocytes from Pluripotent Stem Cells to Promote Cancer Immunosurveillance," Cancer Research, vol. 71, No. 14, pp. 4742-4747.

Duda et al. (2014) "High-efficiency genome editing via 2A-coupled co-expression of fluorescent proteins and zinc finger nucleases or CRISPRjCas9 nickase pairs," Nucleic Acids Research, vol. 42, No. 10, 16 pp.

Nishimura et al. (2013) "Generation of Rejuvenated Antigen-Specific T Cells by Reprogramming to Pluripotency and Redifferentiation," Cell Stem Cell, vol. 12, No. 1, pp. 114-126.

English translation of International Preliminary Report on Patentability for PCT/JP2015/070608 mailed on Jan. 24, 2017.

Extended European Search Report issued in the corresponding EP Application No. 15821273.8 mailed on Feb. 2, 2018, 7 pp.

International Search Report and Written Opinion of PCT/JP2015/070608 mailed Oct. 20, 2015, 10 pp.

Hale et al. (2010) "Cutting Edge: Rag Deletion in Peripheral T Cells Blocks TCR Revision," J. Immunol. 184:5964-5968.

Mombaerts et al. (1992) "RAG-1-deficient mice have no mature B and T lymphocytes," Cell. 68:869-877.

(56) References Cited

OTHER PUBLICATIONS

Shinkai et al. (1992) "RAG-2-deficient mice lack mature lymphocytes owing to inability to initiate V(D)J rearrangement," Cell. 68:855-867.

Turka et al. (1991) "Thymocyte expression of RAG-1 and RAG-2: termination by T cell receptor cross-linking," Science. 253:778-781.

Watanabe et al. (Feb. 2013) "Establishment of a stable T lymphoma cell line transduced with HLA-A*24:02-restricted WT1-specific TCR genes and its application to antigen-specific immunomonitoring," Biomed. Res. 34(1):41-50.

International Search Report with Written Opinion corresponding to International Patent Application No. PCT/JP2015/070608, mailed Oct. 28, 2015.

Minagawa et al., "Enhancing T Cell Receptor Stability in Rejuvenated Ipsc-Derived T Cells Improves Their Use in Cancer Immunotherapy", Cell Stem Cell vol. 23, pp. 850-858, Dec. 6, 2018.

Riolobos et al., "HLA Engineering of Human Pluripotent Stem Cells", Molecular Therapy, vol. 21, No. 6, pp. 1232-1241, Jun. 2013.

Themeli et al., "Generation of tumor-targeted human T lymphocytes from induce pluripotent stem cells for cancer therapy", Nature Biotechnology, vol. 31, No. 10, pp. 928-933 doi: 10.1038/nbt.2678.

Maeda et al., "Regeneration of CD8aβ T Cells from T-cell-Derived iPSC Imparts Potent Tumor Antigen-Specific Cytotoxicity", Cancer Research, Dec. 1, 2016, vol. 76, No. 23, pp. 6839-6850.

Shlyahtenko et al., "Molecular Mechanism Underlying RAG1/RAG2 Synaptic Complex Formation." The Journal of Biological Chemistry 284(31):20956-20964 (2009).

Cheroutre et al., "Doubting the TCR Coreceptor Function of CD8aa." Immunity 28:149-159 (2008).

Parel et al., "CD4+ CD8+ double positive (DP) T cells in health and disease." Autoimmunity Reviews 3:215-220 (2004).

McMahan et al., "RAG Reexpression and DNA Recombination at T Cell Receptor Loci in Peripheral CD4+ T Cells," Immunity, 9:637-647, 1998.

Michie et al., "Allelic exclusion and differentiation by protein kinase C-mediated signals in immature thymocytes," Proc. Natl. Acad. Sci., 98(2):609-614, 2001.

Minagawa et al., "Enhancing T Cell Receptor Stability in Rejuvenated iPSC-Derived T Cells Improves Their Use in Cancer Immunotherapy," Cell Stem Cell, 23:850-858, 2018.

Shinkai et al., "RAG-2-Deficient Mice Lack Mature Lymphocytes Owing to Inability to Initiate V(D)J Rearrangement," Cell, 68:855-867, 1992.

Villa et al., "V(D)J recombination defects in lymphocytes due to RAG mutations: severe immunodeficiency with a spectrum of clinical presentations," Blood, 97(1):81-88, 2001.

* cited by examiner

P value = 0.029

METHOD FOR INDUCING T CELLS FOR CELL-BASED IMMUNOTHERAPY FROM PLURIPOTENT STEM CELLS

RELATED APPLICATIONS

This application is a 35 U.S.C. § 371 filing of International Application No. PCT/JP2015/070608, filed Jul. 17, 2015, which claims priority to U.S. Provisional Patent Application Nos. 62/026,332 and 62/026,341, each filed Jul. 18, 2014. The content of each of these applications is incorporated herein by reference in its entirety.

TECHNICAL FIELD

The present application relates to a method for inducing T cells that are used for cell-based immunotherapy. Especially, a method for efficiently and surely inducing T cells bearing desired antigen specific T cell receptor genes from pluripotent stem cells, such as iPS cells is provided. The present application further relates to a method for creating a cell bank utilizing the iPS cells and is effectively used for a cell-based immunotherapy.

Each T cell expresses a T cell receptor (TCR) with different specificity. When an infectious disease develops, a T cell having a suitable specificity will proliferate to give a T cell population (clone) that will fight with the pathogen. This is the basic idea of the acquired immunity. If it is possible to artificially amplify a T cell bearing a TCR specific for a desired antigen, the amplified T cells may be used for adoptive immunotherapy. The amplification of a specific T cell is called as "cloning". In fact, autologous transplantation of antigen specific T cells prepared by amplifying the antigen specific T cell obtained from the patient has been clinically conducted. However, almost all autologous T cell transplantation therapy do not use a cell population purified to the extent of "cloned" cells. In addition, repeated in vitro subcultur of the cells might cause loss of the function to kill the cancer cells.

A method for providing T cells that are capable of infinitely proliferating by immortalizing the cells has been proposed. A cell may be immortalized and proliferated to give a cloned cell population. Procedures to immortalize a cell may include fusion of the cell with a cancer cell as well as long term culture of the cells with stimulating TCR under the presence of cytokines. However, auto-transplantation of thus obtained immortalized T cells may be dangerous. In addition, the cloning procedures could lower the cell function.

A cell-based immunotherapy in which iPS cells are established from a human T cell, T cells having the rearranged TCR genes that are the same as those in the original human T cell from which the iPS cells were induced are re-generated from the iPS cells, and the re-generated T cells are used for the treatment has been proposed (WO 2013/176197 A1 and Vizcardo et al. Cell Stem Cell 12,31-36 2013, and Nishimura T et al. Cell Stem Cell, 2013).

iPS cells may be established from a human T cell and re-differentiated into mature T cells according to the procedures taught by above discussed references. During the differentiation of the iPS cells into mature T cells, the TCR$\alpha$ chain is subjected to additional rearrangement. (Nishimura T et al. Cell Stem Cell, 2013). This additional TCR$\alpha$ gene rearrangement not only results in loss of specificity of the TCR but also the possibility of producing autoreactive T cells by mispairing with unintended chain. When self-reactive T cells are generated, extremely dangerous reactions that damage normal tissues may occur.

A project to create a highly versatile iPS cell bank with donors having HLA haplotypes that are frequently found in Japanese people in homozygous is in progress. (CURANOSKI, Nature vol. 488, 139 (2012) and Shin Kaneko, The Medical Frontline 69:724-733, 2014). As for T cells, transplantation from a donor with a homozygous HLA haplotype to a recipient with heterozygous HLA haplotypes (allogenic transplantation) has been regarded as an absolute contraindication. Therefore, a concept of a cell based immunotherapy in which mature T cells with desired TCR that are re-generated from iPS cells selected from the iPS cell bank are used has been deemed negative. From the recipient's immune system, donor's T cells are autologous (autograft) when the recipient has heterozygous HLA haplotypes and the donor has a homozygous HLA haplotype, but from the donor's T cells, recipient's somatic cells are non-self (allograft). For this reason, there is a report of a risk of causing severe graft-versus-host reactions leading to death of the recipient (Ito et al. Lancet. 331:413.1988).

CITATION LIST

Patent Literature

Patent Literature 1: WO2013/176197 A1

Patent Literature 2: WO2011/096482 A1

Non-Patent Literature

Non-Patent Literature 1: Vizcardo et al. Cell Stem Cell. 12:31-36. 2013

Non-Patent Literature 2: Nishimura T et al. Cell Stem Cell. 12:114-226.2013

Non-Patent Literature 3: Ito et al. Lancet. 331:413.1988

Non-Patent Literature 4: Bendle GM et al. Nat. Med. 16(5): 565-70.2010

Non-Patent Literature 5: Cyranoski, Nature. 488:139.2012

Non-Patent Literature 6: Shin Kaneko. The Medical Frontline. 69:724-733.2014

Non-Patent Literature 7: Le Cong et al. Science. 39:819.2013

Non-Patent Literature 8: Prashant Mali et al. Science. 39:823.2013

SUMMARY OF INVENTION

The present application provides a method for inducing a T cell clone bearing a desired TCR from pluripotent stem cells. The application also provides a method for creating a cell bank for a cell-based immunotherapy from iPS cells and a cell bank for a cell-based immunotherapy.

In one embodiment, the present application provides a method for inducing T cells for a cell-based immunotherapy, comprising the steps of:

(1) providing Rag1 and/or Rag2 gene knockout human pluripotent stem cells bearing genes encoding a T cell receptor (TCR) specific for a desired antigen, and (2) inducing T cells from the pluripotent stem cells of step (1).

In this embodiment, "Rag1 and/or Rag2 knockout human pluripotent stem cells bearing genes encoding a T cell receptor (TCR) specific for a desired antigen" may be prepared by a method comprising the steps of:

(a) inducing pluripotent stem cells bearing genes encoding the antigen specific TCR, and (b) knocking out Rag1 and/or Rag2 gene of the pluripotent stem cells by genome editing. In this embodiment, pluripotent stem cells bearing genes encoding the antigen specific TCR may be obtained by inducing pluripotent stem cells from a T cell bearing the desired TCR. Alternatively, genes encoding the antigen specific TCR may be introduced into the pluripotent stem cells.

Alternatively, "Rag1 and/or Rag2 knockout human pluripotent stem cells bearing genes encoding a TCR specific for a desired antigen" may be prepared by knocking out Rag1 and/or Rag2 gene in the pluripotent stem cells by genome editing and then, introducing genes encoding the antigen specific TCR into the Rag1 and/or Rag2 knockout cells.

In this application, Rag1 and/Rag2 gene may be knocked out by introducing frame shift mutation in both alleles by genome editing, especially, genome editing using CRISPER-Cas 9 or TALEN system. Rag1 and/or Rag2 gene may also be knocked out by means of homologous recombination.

By knocking out Rag1 and/or Rag2 gene in the pluripotent stem cells, rearrangement of the TCR will not or unlikely occur during the differentiation of the pluripotent stem cells bearing the desired TCR into T cells. Accordingly, the T cells for a cell-based immunotherapy provided by this embodiment will be monoclone cells bearing the desired TCR and therefore, can be used for conducting safe and effective immunotherapy.

In another embodiment of the present application, an iPS cell bank for a cell-based immunotherapy, wherein Rag1 or Rag2 knockout iPS cells derived from donors with a homozygous HLA haplotype are stored in connection with information regarding HLA of each donor will be provided.

A project for creating an iPS cell stock involving iPS cells established from cells derived from healthy volunteers with a homozygous HLA haplotype, i.e. iPS cells less likely exert rejection reaction (Shin Kaneko, The Medical Frontline. 69:724-733.2014.), is now in progress. iPS cells used in the 2nd embodiment may be obtained from the iPS cell stock in which iPS cells are stocked in connection with HLA information of each healthy volunteer from whom said iPS cells had been established.

The iPS cell bank for a cell-based immunotherapy of this embodiment may be used in various types of immunotherapy. When used in a cell-based immunotherapy, iPS cells established from a HLA-matched donor, i.e. at least one HLA haplotype of the subject to be treated match the donor's a homozygous HLA haplotype, are selected and genes encoding a TCR for the treatment are introduced into the selected iPS cells. The TCR-introduced iPS cells are then differentiated into T cells to give T cells for the cell-based immunotherapy suitable for the subject.

In a still further embodiment, a method for creating an iPS cell bank for a cell-based immunotherapy, which comprises the steps of: (1) providing iPS cells established from cells derived from donors with a homozygous HLA haplotype, (2) knocking out Rag1 and/or Rag2 gene in the iPS cells by genome editing, (3) introducing genes encoding a desired TCR into the Rag1 and/or Rag2 gene knockout iPS cells obtained in step (2), and storing the iPS cells with information of HLA of each donor and the introduced genes encoding the TCR. In this method, iPS cells introduced with TCR genes useful for the treatment are stored. According to this embodiment, T cells for the cell-based immunotherapy can be provided quickly.

In a still further embodiment, a method for inducing T cells for a cell-based immunotherapy, which comprises the steps of: (1) selecting iPS cells established from a cell of a donor having a homozygous HLA haplotype that matches at least one HLA haplotype of the subject to be treated, from an iPS cell bank in which iPS cells established from cells derived from donors having a homozygous HLA haplotype are stored in connection with information regarding HLA of each donor, (2) knocking out Rag1 and/or Rag2 gene in the selected iPS cells by genome editing, (3) introducing genes encoding a desired TCR into the Rag1 and/or Rag2 gene knockout iPS cells obtained in step (2), and (4) differentiating the TCR introduced Rag1 and/or Rag2 knockout iPS cells into T cells.

In a still further embodiment, a cell-based immunotherapy method, which comprises administering the T cells obtained by the method for inducing T cells for a cell-based immunotherapy provided by the present application to a subject in need thereof is provided.

By knocking out Rag1 and/or Rag2 gene in the pluripotent stem cells bearing the desired TCR genes, TCR-rearrangement during the differentiation from the pluripotent stem cells into T cells are blocked or well suppressed. T cells induced by this method are used as clonally expanded cells bearing the desired TCR.

In a further embodiment, a cell-based immunotherapy method which comprises inducing T cell progenitors or mature T cells from pluripotent stem cells bearing genes encoding a TCR specific for a desired antigen that are established from a cell of a donor with a homozygous HLA haplotype, and administering the obtained T cell progenitors or mature T cells to a recipient one or both of whose HLA haplotype matches the donor's HLA haplotype is provided. Further, the present application provides an iPS cell bank in which iPS cells bearing genes encoding a TCR specific for a desired antigen that are established from a cell of a donor with a homozygous HLA haplotype are stored in connection with information regarding HLA of each donor and the TCR.

In the case of allogeneic transplantation, it is almost impossible to find a donor whose HLAs are completely identical to those of the recipient. Once T cells are transplanted, donor T cells may recognize HLA mismatch as an attack target. As a result, a so-called graft-versus-host reaction occurs, in which a part of the transplanted donor T cells attack the recipient's cells.

In contrast, T cells induced by the method of the present application are clonally expanded cells with a single TCR and exert single T cell specificity. Thus, even if the cells derived from a donor with a homozygous HLA haplotype are transplanted into a recipient with heterologous HLA haplotypes one of which matches the donor's HLA haplotype (allogenic transplantation), the possibility of causing a graft versus host reaction is significantly low.

EMBODIMENT OF THE INVENTION

Figure 1:
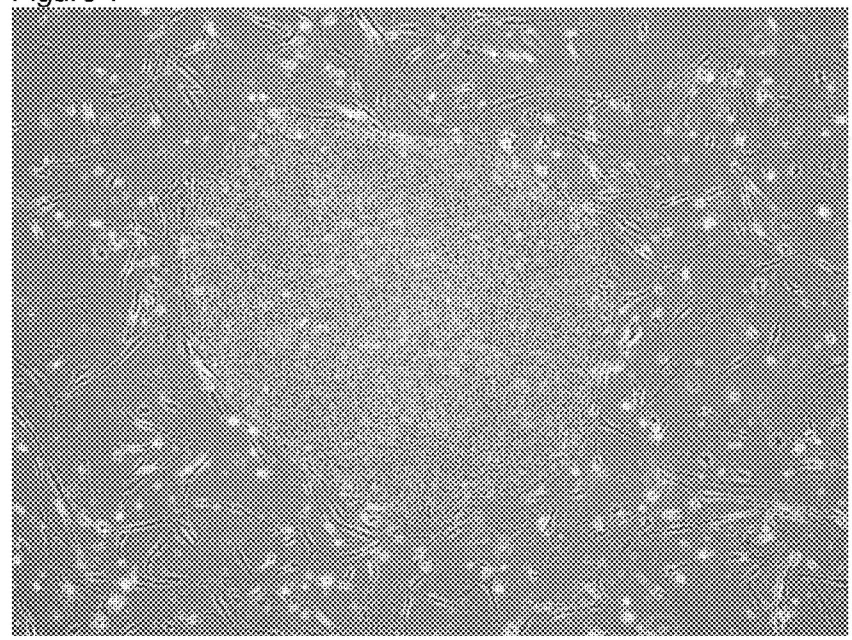
FIG. 1 is a photograph of iPS cell colony established in Example 1.

In this application, provided is a method for inducing T cells for a cell-based immunotherapy, comprising the steps of:

(1) providing Rag1 and/or Rag2 gene knockout human pluripotent stem cells bearing genes encoding a T cell receptor (TCR) specific for a desired antigen, and (2) inducing T cells from the pluripotent stem cells of step (1).

In the specification and claims, "pluripotent stem cells" refer to stem cells having pluripotency, i.e. an ability to differentiate into many types of cells in the body, and self-propagation ability. Examples of pluripotent stem cells may include embryonic stem cells (ES cells), nuclear transfer embryonic stem cells (ntES cells), germline stem cells (GS cells), embryonic germ cells (EG cells), induced pluripotent stem cells (iPS cells), and pluripotent cells derived from cultured fibroblasts and bone marrow stem cells (Muse cells). iPS cells and Muse cells are preferable in view of the fact that those pluripotent stem cells can be obtained by not destroying the embryos. The pluripotent stem cells are preferably those derived from mammal and more preferably, are human pluripotent stem cells. iPS cells are preferably used.

In one embodiment, the Rag1 and/or Rag2 knockout human pluripotent stem cells bearing genes encoding a TCR specific for a desired antigen may be obtained by establishing iPS cells from a human T cell bearing the desired TCR and then, knocking out Rag1 and/or Rag2 gene in the established iPS cells (T-iPS cells).

In the specification and claims, "T cells" refer to cells expressing receptors for antigens called as T cell receptor (TCR). The fact that TCR of a T cell is maintained in iPS cells established from the T cell has been reported by WO2011/096482, Vizcardo et al. Cell Stem Cell 12, 31-36 2013 and Nishimura T et al. Cell Stem Cell, 114-126, 2013.

T cells used as origin for iPS cells may preferably be T cells expressing at least one of CD4 and CD8, in addition to CD3. Examples of the preferable human T cells may include helper/regulatory T cells that are CD4 positive cells; cytotoxic T cells that are CD8 positive cells; naive T cells that are CD45RA$^{|}$CD62L$^{|}$ cells; central memory T cells that are CD45RA$^{-}$CD62L$^{+}$ cells, effector memory T cells that are CD45RA$^{-}$CD62L$^{-}$ cells and terminal effector T cells that are CD45RA$^{+}$CD62L$^{-}$ $^{cells.}$ Human T cells can be isolated from a human tissue by known procedures. The human tissue is not limited in particular, as long as the tissue contains T cells of the above-mentioned type, and examples thereof include peripheral blood, lymph node, bone marrow, thymus, spleen, umbilical cord blood, and a lesion site tissue. Among these, peripheral blood and umbilical cord blood are preferable since they can be derived less invasively from the human body and can be prepared with ease. Known procedures for isolating human T cells include, for example, flow cytometry using an antibody directing to a cell surface marker, such as CD4, and a cell sorter, as shown in the below-mentioned Examples. Alternatively, desired T cells can be isolated by detecting the secretion of a cytokine or the expression of a functional molecule as an indicator. In this case, for example, T cells secrete different cytokines, depending on whether they are of the Th1 or Th2 type, and thus T cells of a desired Th type can be isolated by selecting T cells using the cytokine as an indicator. Similarly, cytotoxic (killer) T cells can be isolated using the secretion or production of granzyme, perforin, or the like as an indicator.

"A T cell bearing a TCR specific for a desired antigen" may be a cytotoxic T lymphocyte having the TCR obtained from or derived from a donor. For example, cytotoxic T lymphocytes specific for a cancer antigen may be prepared by co-culturing the lymphocytes obtained from the donor by a conventional procedure with a cancer antigen specific for the cancer to be treated. Cancer antigens have been identified for variety of cancers and procedures for inducing cytotoxic T lymphocytes with a cancer antigen or an epitope peptide thereof have been well known. Alternatively, the lymphocytes may be co-cultured with cells of the cancer to be treated.

Alternatively, cytotoxic T lymphocytes specific for a cancer antigen of a cancer to be treated may be induced from peripheral blood of a subject who is suffered from the cancer.

"Human T cells specific for a desired antigen" may be isolated from human cell culture or human tissue containing T cells specific for the antigen by using a tetramer of the antigen-bound major histocompatibility complex (MHC tetramer).

Induced pluripotent stem (iPS) cells can be prepared by introducing specific reprogramming factors to somatic cells. iPS cells are somatic cell-derived artificial stem cells having properties almost equivalent to those of ES cells (K. Takahashi and S. Yamanaka. Cell. 126:663-676.2006; K. Takahashi et al. Cell. 131:861-872.2007; J. Yu et al. Science. 318:1917-1920.2007; Nakagawa M. et al. Nat. Biotechnol. 26:101-106.2008; and WO 2007/069666). The reprogramming factors may be constituted by genes or gene products thereof, or non-coding RNAs, which are expressed specifically in ES cells; or genes or gene products thereof, non-coding RNAs or low molecular weight compounds, which play important roles in maintenance of the undifferentiated state of ES cells. Examples of genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tell, beta-catenin, Lin28b, Sall1, Sall4, Esrrb, Nr5a2, Tbx3 and Glis1, and these reprogramming factors may be used either individually or in combination. Examples of the combination of the reprogramming factors include those described in WO2007/069666; WO2008/1 18820; WO2009/007852; WO2009/032194; WO2009/058413; WO2009/057831; WO2009/075119; WO2009/079007; WO2009/091659; WO2009/101084; WO2009/101407; WO2009/102983; WO2009/1 14949; WO2009/1 17439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/11 1409; WO 2010/1 11422; WO2010/1 15050; WO2010/124290; WO2010/147395; WO2010/147612; Huangfu D et al. Nat. Biotechnol. 26:795-797.2008; Shi Y et al. Cell Stem Cell. 2:525-5283.2008; Eminli S et al. Stem Cells. 26:2467-2474.2008; Huangfu D et al. Nat Biotechnol. 26:1269-1275.2008; Shi Y et al. Cell Stem Cell. 3:568-574.2008; Zhao Y et al. Cell Stem Cell. 3:475-479.2008; Marson A. Cell Stem Cell. 3:132-135.2008; Feng B et al. Nat Cell Biol. 1 1:197-203.2008; R. L. Judson et al. Nat. Biotech. 27:459-461.2009; Lyssiotis C A et al. Proc Natl Acad Sci USA. 106:8912-8917.2009; Kim J B et al. Nature. 461:649-643.2009; Ichida J K et al. Cell Stem Cell. 5:491-503.2009; Heng J C et al. Cell Stem Cell. 6:167-74.2009; Han J et al. Nature. 463:1096-100.2010; Mali P et al. Stem Cells. 28:713-720.2010, and Maekawa M, et al. Nature. 474:225-9.2011. The contents of the documents cited in this paragraph are herein incorporated by reference.

The reprogramming factors may be contacted with or introduced into the somatic cells by a known procedure suitable for the form of the factor to be used.

In the case where the reprogramming factors are in the form of protein, the reprogramming factors may be introduced into somatic cells by a method such as lipofection, fusion with a cell-permeable peptide (e.g., HIV-derived TAT or polyarginine), or microinjection.

In the case where the reprogramming factors are in the form of DNA, the reprogramming factors may be introduced into somatic cells by a method such as use of a vector including virus, plasmid and artificial chromosome vectors; lipofection; use of liposome; or microinjection. Examples of the virus vector include retrovirus vectors, lentivirus vectors (these are described in Cell. 126:663-676.2006; Cell. 131:861-872.2007; and Science. 318:1917-1920, 2007), adenovirus vectors (Science. 322:945-949.2008), adeno-associated virus vectors and Sendai virus vectors (WO 2010/008054). Examples of the artificial chromosome vector include human artificial chromosome (HAC), yeast artificial chromosome (YAC), and bacterial artificial chromosome (BAC and PAC). Examples of the plasmid which may be used include plasmids for mammalian cells (Science, 322:949-953, 2008). The vector may contain a regulatory sequence(s) such as a promoter, enhancer, ribosome binding sequence, terminator and/or polyadenylation site to enable expression of the nuclear reprogramming factors; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG. Further, in order to remove, after introduction of the gene into the somatic cells and expression of the same, the genes encoding the reprogramming factors, or both the promoter(s) and the genes encoding the reprogramming factors linked thereto, the vector may have LoxP sequences upstream and downstream of these sequences.

Further, in the case where the reprogramming factors are in the form of RNA, each reprogramming factor may be introduced into somatic cells by a method such as lipofection or microinjection, and an RNA into which 5-methylcytidine and pseudouridine (TriLink Biotechnologies) were incorporated may be used in order to suppress degradation (Warren L. Cell Stem Cell. 7:618-630.2010). The documents cited in this paragraph are herein incorporated by reference.

Examples of the medium for inducing iPS cells include DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the method to induce iPS cells include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing ES-like colonies to appear about 30 to about 45 days after the contact, or later.

Alternatively, the cells may be contacted with the reprogramming factors and cultured at 37° C. in the presence of 5% $CO_2$ on feeder cells (e.g., mitomycin C-treated STO cells or SNL cells) in DMEM medium supplemented with 10% FBS (this medium may further contain LIF, penicillin/streptomycin, puromycin, L-glutamine, non-essential amino acids, β-mercaptoethanol and the like, as appropriate) for about 25 to about 30 days or longer, thereby allowing ES-like colonies to appear. Preferred examples of the culture method include a method wherein the somatic cells themselves to be reprogrammed are used instead of the feeder cells (Takahashi K et al. PLoS One. 4:e8067.2009 or WO2010/137746), and a method wherein an extracellular matrix (e.g., Laminin-5 (WO2009/123349), Laminin-5 (WO2009/123349), Laminin-10 (US2008/0213885) or its fragment (WO2011/043405) or Matrigel (BD)) is used instead. The documents cited in this paragraph are herein incorporated by reference.

Other examples include a method wherein the iPS cells are established using a serum-free medium (Sun N et al. Proc Natl Acad Sci USA. 106:15720-15725.2009). Further, in order to enhance the establishment efficiency, iPS cells may be established under low oxygen conditions (at an oxygen concentration of 0.1% to 15%) (Yoshida Y et al. Cell Stem Cell. 5:237-241.2009 or WO2010/013845). The contents of the documents cited in this paragraph are herein incorporated by reference.

Examples of factors used for enhancing the establishment efficiency may include histone deacetylase (HDAC) inhibitors [e.g., low molecular inhibitors such as valproic acid (VPA), trichostatin A, sodium butyrate, MC1293, and M344, nucleic acid-based expression inhibitors such as siRNAs and shRNAs against HDAC (e.g., HDAC1 siRNA Smartpool, registered trademark (Millipore)), HuSH 29mer shRNA Constructs against HDAC1 (OriGene) and the like), and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, Suv39h2, SetDB1 and G9a], L-channel calcium agonist (for example, Bayk8644), butyric acid, TGFβ inhibitor or ALK5 inhibitor (e.g., LY364947, SB431542, 616453 and A-83-01), p53 inhibitor (for example, siRNA and shRNA against p53), ARID3A inhibitor (e.g., siRNA and shRNA against ARID3A), miRNA such as miR-291-3p, miR-294, miR-295, mir-302 and the like, Wnt Signaling (for example, soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. Upon establishing iPS cells, a medium added with the factor for enhancing the establishment efficiency may be used.

During the culture, the medium is replaced with the fresh medium once every day from Day 2 of the culture. The number of somatic cells used for nuclear reprogramming is not restricted, and usually within the range of about $5\times10^3$ to about $5\times10^6$ cells per 100 $cm^2$ area on the culture plate.

iPS cells may be selected based on the shape of each formed colony. In cases where a drug resistance gene is introduced as a marker gene such that the drug resistance gene is expressed in conjunction with a gene that is expressed when a somatic cell was reprogrammed (e.g., Oct3/4 or Nanog), the established iPS cells can be selected by culturing the cells in a medium containing the corresponding drug (selection medium). Further, iPS cells can be selected by observation under a fluorescence microscope in cases where the marker gene is the gene of a fluorescent protein.

Rag1 and/or Rag2 gene may be knocked out from T-iPS cells by genome editing according to a known procedure such as those taught by Le Cong et al. Science 39; 819, 2013 or Prashant Mali et al. Science 39; 823, 2013, by using a known genome editing system such as CRISPER-Cas9 or TALEN or by means of homologous recombination.

CRISPER-Cas9 is a simple and effective method of genome editing to introduce mutation that causes a functional defect in a specific part of a genome. A target gene can be inactivated by preparing a single-guide RNA (sgRNA) targeting the specific part of the genome, causing cut the double stranded DNA by delivering the Cas9 nuclease to the part of the genome to which the sgRNA is attached, and then, causing frame shift indel mutation that inactivates the targeted gene function. Rag1 and/Rag2 knockout may be effected by means of any one of known genome editing procedures.

In another embodiment, "Rag1 and/or Rag2 knockout human pluripotent stem cells bearing a TCR specific for a desired antigen" may be prepared by knocking out the Rag1 and/or Rag 2 genes from the human pluripotent stem cells by genome editing and then, introducing genes encoding the antigen specific TCR into the Rag 1 and/or Rag 2 knockout human pluripotent stem cells.

In this embodiment, the human pluripotent stem cells may be iPS cells established from somatic cells of a subject to be treated by the immunotherapy, or iPS cells established from somatic cells of a person having HLAs that match the HLAs of the subject to a predetermined extent. Alternatively, the iPS cells may be selected from those previously established from somatic cells of donors and stored in connection with information regarding HLAs of each donor.

For example, iPS cells may be those having an HLA haplotype that matches at least one of the HLA haplotypes of the subject to be treated and selected from an iPS cell bank in which iPS cells established from cells of donors with a homozygous HLA haplotype are stored in connection with information regarding HLA of each donor.

The term "somatic cells" used in the specification and claims means any animal cells (preferably cells of a mammal including human) other than germ-line cells or pluripotent cells (other than the cells such as sperms, spermatocytes, eggs, oocytes and ES cells). Examples of the somatic cells include, but are not limited to, any of fetal somatic cells, neonatal somatic cells, and mature, healthy and diseased somatic cells, as well as any of primary cultured cells, subcultured cells and established cell lines. Specific examples of the somatic cells include, but not limited to, (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and adipocytes. In view of the low invasiveness, cells derived from peripheral blood, skin and umbilical cord blood are preferably used.

Rag2 gene in the iPS cell may be knocked out in the same manner as the above explained procedures for knocking out the Rag1 and/or Rag2 gene from the T-iPS cells.

Genes encoding a TCR specific for a desired antigen are introduced into the Rag1 and/or Rag2 knockout iPS cells.

Genes encoding TCRs specific for various cancer antigens have been reported. TCR genes may be obtained from T cells specific for the desired antigen isolated from a patient having a cancer or an infectious disease. The TCR genes may be isolated from thus obtained T cells. In this application, genes encoding the antigen specific TCR may be introduced into iPS cells that were established from a donor cell. For example, this procedure may be conducted as taught by Morgan R. A. et al. Science, 314:126. 2006 (this document is herein incorporated by reference). In particular, a suitable vector containing the TCR genes may be introduced into the iPS cells. For example, TCR genes may be introduced by a vector such as virus, plasmid and artificial chromosome vectors; or by means of lipofection, liposome or microinjection. Examples of the virus vectors include retrovirus vectors, lentivirus vectors, adenovirus vectors, adeno-associated virus vectors, and Sendai virus vectors. Examples of the artificial chromosome vector include human artificial chromosome (HAC), yeast artificial chromosome (YAC), and bacterial artificial chromosome (BAC and PAC). Examples of the plasmid which may be used include plasmids for mammalian cells. The vector may contain a regulatory sequence(s) such as a promoter, enhancer, ribosome binding sequence, terminator and/or polyadenylation site to enable expression of the TCR genes. If desired, the vector may also contain a selection marker such as a drug resistance gene (e.g., kanamycin-resistant gene, ampicillin-resistant gene or puromycin-resistant gene), thymidine kinase gene or diphtheria toxin gene; and a reporter such as the green-fluorescent protein (GFP), β-glucuronidase (GUS) or FLAG.

In this specification, iPS cells obtained by introducing the TCR genes are called as "TCR-iPS cells". T cells are differentiated from Rag1 and/or Rag2 knockout T-iPS or TCR-iPS cells. The procedure for differentiating pluripotent stem cells into T cells may be that taught by Timmermans et al. Journal of Immunology, 2009, 182:6879-6888, Nishimura T et al. 2013, Cell Stem Cell 114-126, WO 2013176197 A1 and WO 2011096482 A1.

T cells are roughly divided into αβ T cells and γδ T cells. αβ T cells include killer T cells and helper T cells. In this specification and claims "T cells differentiated from iPS cells" cover all types of T cells. T cells may cover any of T progenitor cells and mature T cells. Preferably, T cells may be those expressing at least one of CD4 and CD8, in addition to CD3.

In various therapies proposed up to now wherein various cells or tissues, other than T cells, that are differentiated from iPS cells are transplanted, the cells to be transplanted are expected to be fixed in the body of the patient for his/her entire life. In regenerative therapies that use cells or tissues re-generated from iPS cell stock for allogenic transplantation, the patients need to take immune suppressing drugs for their entire life.

On the other hand, allogenic graft will be eventually rejected due to mismatches of minor histocompatibility antigens even in the HLA-matched donor and recipient. In this point, the cell-based immunotherapy provided by this application is unexpectedly advantageous than the other allogenic transplantation of the cells or tissues re-generated from iPS cells.

In one embodiment of the present application, an iPS cell bank for a cell-based immunotherapy is provided. The iPS cell bank may be created by using cells derived from donors with a homozygous HLA haplotype. The iPS cell bank may be those storing Rag2 knockout iPS cells obtained by establishing iPS cells from the cells of donors with a homozygous HLA haplotype and knocking out Rag1 and/or Rag2 gene in the iPS cells in connection with information regarding HLAs of each donor.

Alternatively, the cell bank for the cell-based immunotherapy may be those storing T cell progenitors or mature T cells re-generated from the T-iPS cells or TCR-iPS cells. The merits of storing the re-generated T cells may be not only the shortening of the time period required for the preparation before starting the therapy but also making it possible to verify the quality of the cells before the transplantation.

In the cell-based immunotherapy of the present application, the re-generated T cells are dispersed in a suitable medium such as saline or PBS and the dispersion may be administered to a patient having HLA haplotypes at least one of which matches the donor's HLA haplotype. The cells may be administered intravenously.

The number of the cells to be administered is not limited and may be determined based on, for example, the age, sex, height and body weight of the patient, disease and conditions to be treated. The optimal cell number may be determined through clinical studies.

T cells may target various antigens and therefore, the method of this application may be applied for a cell-based immunotherapy against various diseases including, but not limited to, cancers, infectious diseases, autoimmune diseases and allergies by selecting a TCR suitable for the therapy.

The present application also provides a method for cell-based immunotherapy which comprises, inducing T cell progenitors or mature T cells induced from iPS cells that were established from a cell of a donor with a homozygous HLA haplotype and administering the T cell progenitors or mature T cells to a patient at least one of whose HLA haplotypes matches the HLA haplotype of the donor. Further, the present application provides an iPS cell bank in which iPS cells bearing genes encoding a TCR specific for a desired antigen established from cells of donors with a homozygous HLA haplotype in connection with information regarding HLA of each donor.

As shown by Examples 4 and 5, it is possible to regenerate T cells that maintain the antigen specificity of the original T cell from which the T-iPS cells were established, by giving the stimulation with the antigen at early stages of the differentiation from T-iPS cells into T cells even if Rag1 and/or Rag2 gene is not knocked out from the T-iPS cells. In this application, an iPS cell bank created from T-iPS cells or TCR-iPS cells without knocking out Rag1 and/or Rag2 gene is also provided. The application will be explained in more detail with the examples shown below.

EXAMPLE 1

Establishment of iPS cells from a T cell with a homozygous HLA haplotype and Regeneration of T cells from thus obtained iPS cells.

Peripheral blood obtained from a donor having HLA-A*3303-B*4403-C*1403-ERB1*1302 homozygote were used.

1) Establishment of Homo-T-iPS Cells

The medium used were as follows:

TABLE 1

| Medium for T cells (T cell medium): | | |
|---|---|---|
| | Amount | Final conc. |
| RPMI | 45 ml | |
| human AB serum | 5 ml | 10% |
| Total | 50 ml | |

A. Activation of CD8 Positive T Cells

1. Peripheral blood mononuclear cells obtained from the healthy volunteer were purified by using Ficoll and CD8 positive cells were enriched by using MACS beads.

2. The enriched cells were dispersed in the T cell medium and added with IL-2 (final concentration: 30 U/mL), IL-7 (final concentration: 5 ng/mL), and IL-15 (final concentration: 1 ng/mL). Dynabeads Human T-Activator CD3/CD28 was added to give a bead-to-cell ratio of 1:1, and the mixture was incubated for 2 days to activate the CD8 positive cells.

B. Introduction of the Four Yamanaka Factors and SV40 by means of Sendai Virus Vector.

1. The activated CD8 positive cells were dispersed in the T cell medium, Sendai virus bearing the four Yamanaka factors and SV40 was added to the medium and the cell suspension was cultured for 2 days.

2. The obtained cells were washed with the T cell medium and added with the T cell medium supplemented with IL-2 (final concentration: 30 U/mL), IL-7 (final concentration: 5 ng/mL), and IL-15 (final concentration: 1 ng/mL). The cells were further cultured for 2 days.

3. After that, all cells were collected and dispersed in the T cell medium supplemented with IL-2 (final concentration: 30 U/mL). The cell suspension was seeded on the feeder cells.

4. On day 2, a half of the medium was replaced with the fresh iPS cell medium. After that, a half of the medium was replaced with the fresh iPS cell medium every day and the cells were continuously cultured.

C. Picking up iPS Cell Colonies from the Culture

1. Three weeks after the introduction of the Yamanaka factors, colonies of iPS cells were visually observed.

2. Colonies were mechanically picked up with a 200 μl pipette tip.

3. Several clones were established individually. Photograph of the colony of an obtained clone is shown in FIG. 1.

2) Differentiation of T Cells from the iPS Cells.

Media used were as follows:

TABLE 2

| Medium A: for maintenance of OP9 stromal cells | | |
|---|---|---|
| contents | amount added | final conc. |
| αMEM medium | 500 mL | |
| FCS | 125 mL | 20% |
| penicillin-streptomycin solution* | 6.25 mL | 1% |
| Total | 631.25 mL | |

*Mixture of Penicillin (10,000 U/ml) and Streptomycin (10,000 μg/ml). The final concentrations were 100 U/ml and 100 μg/ml, respectively.

TABLE 3

| Medium B: for inducing differentiation of T cells | | |
|---|---|---|
| contents | amount added | final conc. |
| αMEM medium | 500 mL | |
| FCS | 125 mL | 20% |
| penicillin-streptomycin solution* | 5 mL | 1% |
| hrIL-7 (stock: 10 μg/mL) | 315 μL | 5 ng/mL |
| hrFlT-3L (stock: 10 μg/mL) | 315 μL | 5 ng/mL |
| hrSCF (stock: 10 μg/mL) | 630 μL | 10 ng/mL |
| Total | 631.26 mL | |

*Mixture of Penicillin (10,000 U/ml) and Streptomycin (10,000 μg/ml). The final concentrations were 100 U/ml and 100 μg/ml, respectively.

Preparation of OP9 Cells

Six milliliters (6 mL) of 0.1% gelatin solution in PBS was added to a 10 cm dish (Falcon) and incubated for more than 30 minutes at 37° C. OP9 stromal cells were detached from a confluent culture dish with trypsin/EDTA solution and about ¼ of the obtained cells were added to the gelatin-coated 10 cm cell culture dish. 10 mL of medium A was added to the cell culture dish. Four days after, 10 mL of medium A was added to the dish (final amount was 20 mL).

Induction of Hematopoietic Progenitor Cells from iPS Cells

The medium in the OP9 stromal cell culture to be used for the co-culture was aspirated and replaced with fresh medium A. The medium in the human iPS cell culture dish was also aspirated and 10 mL of fresh medium A was added there. The human iPS cell mass was cut with an EZ-passage roller. The cut iPS cell mass was suspended by means of a pipetteman with a 200 μL tip. The number of the iPS cell clusters was visually counted and approximately 600 clusters were seeded on the OP9 cells. Three or more dishes per clone of iPS cells were used, and when subculturing, the cells in all dishes were once pooled in one dish and then redistributed to the same number of dishes to reduce the disparity between the dishes.

Day 1: (the Medium was Replaced)

Whether or not the iPS cell mass adhered to the dish, and the differentiation of the cells were started were observed. The cell culture medium was replaced with 20 mL of fresh medium A.

Day 5: (a Half of the Medium was Replaced)

A half of the cell culture medium was replaced with 10 mL of fresh medium A.

Day 9: (a Half of the Medium was Replaced)

A half of the cell culture medium was replaced with 10 mL of fresh medium A.

Day 13: (Induced Mesodermal Cells were Transferred from OP9 Cell Layer onto OP9/DLL1 Cell Layer)

Cell culture medium was aspirated to remove and the surface of the cultured cells were washed with HBSS(+Mg+Ca) to washout the cell culture medium. 10 mL of Collagenase IV 250U in HBSS (+Mg+Ca) solution was added to the dish and incubated for 45 minutes at 37° C.

The collagenase solution was removed by aspiration and the cells were washed with 10 mL of PBS(−). Then, 0.05% trypsin/EDTA solution was added to the dish and the dish was incubated for 20 minutes at 37° C. After the incubation, the sheet like cell aggregates peeled from the bottom of the dish and the cell aggregates were mechanically fragmented to smaller sizes by means of pipetting. Thus treated cells were added with 20 mL of fresh medium A and cultured for more 45 minutes at 37° C. The culture medium containing the floating cells was passed through a 100 μm mesh and the cells were collected. The cells were then centrifuged at 1200 rpm for 7 minutes at 4° C. The obtained pellet was suspended in 10 mL of medium B. One-tenth of the suspension was separated and used for the FACS analysis. The remaining cell suspension was seeded on new dishes containing OP9/DLL1 cells. Cell suspensions obtained from several dishes were pooled and the pooled cells were then redistributed to the same number of dishes.

Figure 4:
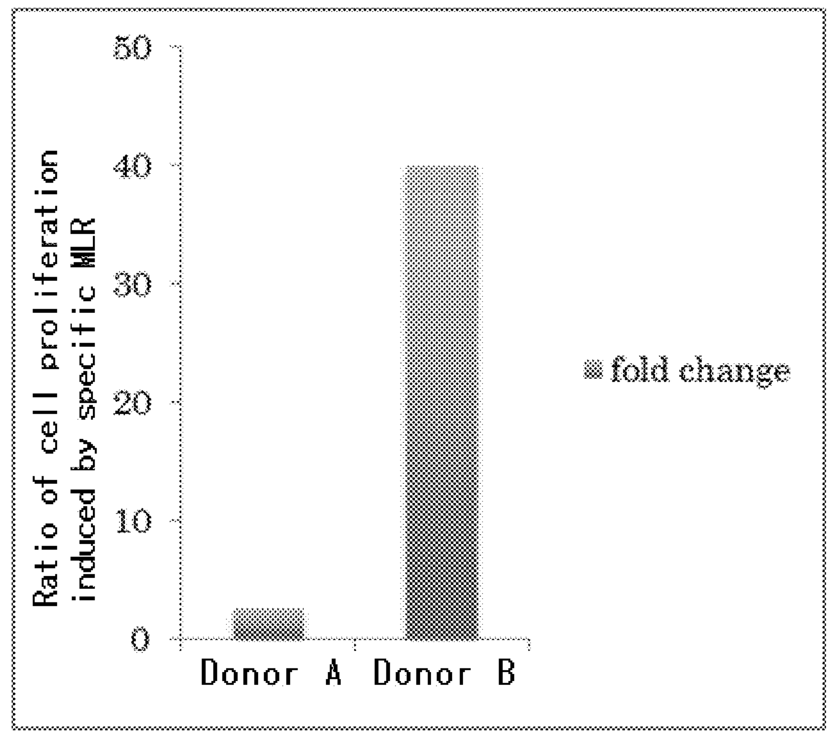
FIG. 4 shows that CD8 positive T cells induced from iPS cells with a homozygous HLA haplotype did not exert the MLR reaction against the cells from donor A having HLA haplotypes one of which matched iPS cells' HLA haplotypes. On the other hand, the T cells exerted the MLR reaction against the T cells of donor B with HLA haplotypes that did not match the iPS cells' HLA haplotypes at all.

In order to ascertain whether or not hematopoietic progenitor cells were contained in the obtained cells, FACS analysis was carried out using anti-CD34 antibody and anti-CD43 antibody. The results are shown in FIG. 4. A sufficient number of cells could be confirmed in the $CD34^{low}CD43^{+}$ cell fraction, and therefore, it was confirmed that hematopoietic progenitor cells were induced.

C. Induction of T Cells from the Hematopoietic Progenitor Cells.

Then, the obtained cells were seeded on new dishes containing OP9/DLL1 cells. In this step, cell sorting for the $CD34^{low}CD43^{+}$ cell fraction was not performed. When this fraction is sorted, the efficiency of differentiation of T cells could be reduced in comparison with the case where sorting is not performed due to the decrease of the cells or damage to the cells by sorting.

During the culturing period, FACS analysis was conducted several times to confirm the differentiation stages. A considerable number of dead cells were observed over the culturing period. Dead cells were preferably eliminated by using, for example, Propidium Iodide (PI) or 7-AAD before the FACS analysis.

Day 16: (Cells were Subcultured)

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on the OP9/DLL1 cells in a new dish.

Day 23: (Cells were Subcultured) Blood Cell Colonies began to appear.

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on new dishes containing OP9/DLL1 cells.

Day 30: (Cells were Subcultured)

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on new dishes containing OP9/DLL1 cells.

Day 37: (Cells were Subcultured)

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on new dishes containing OP9/DLL1 cells.

Day 44: $CD4^{+}CD8^{+}$ T Cells were Confirmed

Figure 2:
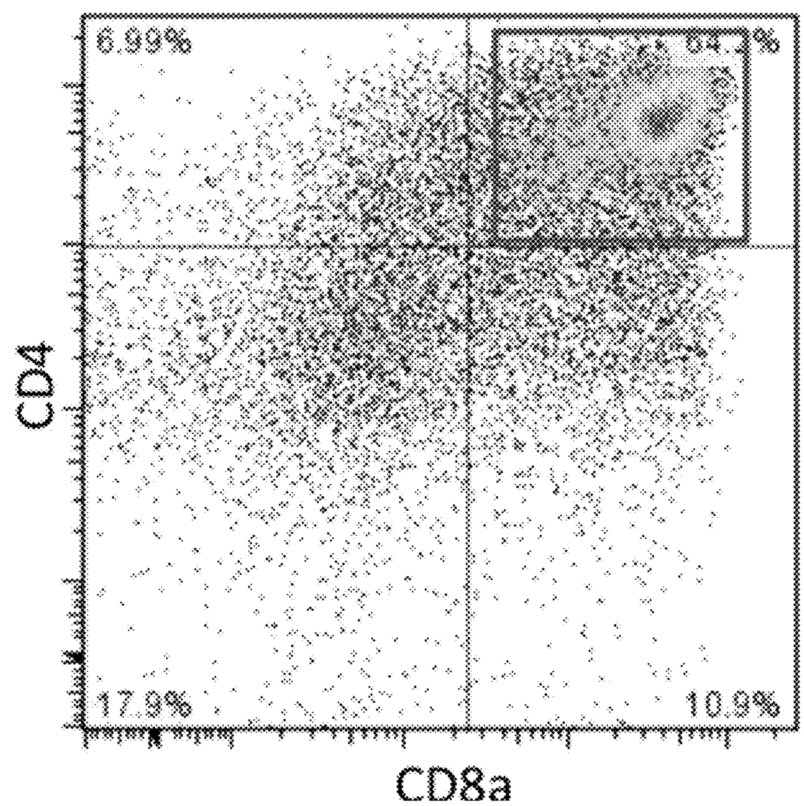
FIG. 2 is a result of FACS analysis that shows CD4CD8 double positive cells were induced from T-iPS cells established from a peripheral blood T cell of a donor with a homozygous HLA haplotype.

In order to confirm T cells were duly induced, the cells on Day 44 were analyzed by FACS with anti CD4 antibody and anti CD8 antibody. Result is shown in FIG. 2. The generation of CD4CD8 double positive cells were confirmed.

As shown above, iPS cells were successfully established from peripheral blood of the donor with a homozygous HLA haplotype and T cells were successfully re-generated from thus obtained iPS cells.

EXAMPLE 2

1. CD8 positive T cells were induced from the T-iPS cells established in Example 1

2. An iPS cell clone with a homozygous HLA haplotype obtained in Example 1 was used. Donor A one of whose HLA haplotypes matches the iPS cell's HLA haplotype, and donor B having HLA haplotypes that do not match the iPS cell's HLA haplotype at all were selected.

DONOR A: HLA-A*31:01/33:03; B*44:03/48:01; C*04:01/14:03; DRB1*04:03/13:02

DONOR B: HLA-A*24:02/24:02; B*07:02/52:01; C*07:02/12:02; DRB1*01:01/15:02

3. Mononuclear cells of Donor A and Donor B were purified from their peripheral blood by using Ficoll and CD8 positive cells were enriched by using CD8 micro beads.

4. Mixed Lymphocyte Reaction (MLR) was conducted by using the CD8 positive T cells re-generated from the T-iPS cells were used as stimulators. The CD8 cells obtained from the donors were used as effectors. Effector cells were fluorescently-labeled by using Cell Trace Violet Cell Proliferation Kit. The stimulator cells were fluorescently-labelled by using Cell Trace CFSF Cell Proliferation Kit.

5. The effector and stimulator cells were mixed so that the effector/stimulator cell ratio was 1:1 ($1\times10^5$ cells each) and the cells were co-cultured for 6 days. On day 3 of the co-culture, IL-2 (12.5 U/mL), IL-7 (5 ng/mL), IL-21 (10 ng/mL) and anti-CD28 antibody (2 ng/mL) were added to the culture medium.

Figure 3:
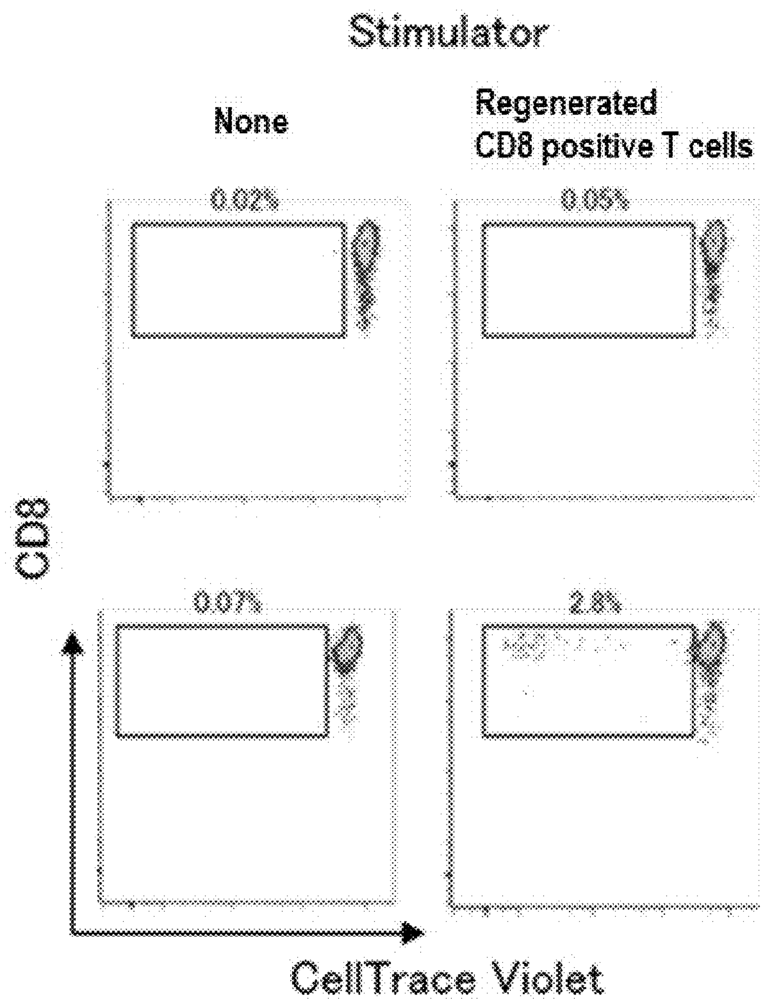
FIG. 3 shows a result of Example 2, wherein CD8 positive T cells induced from T-iPS cells established from a peripheral blood T cell of a donor with a homozygous HLA haplotype were used as stimulator and CD8 positive T cells isolated from peripheral blood mononuclear cells of donors A and B respectively were used as effector cells. Those cells were co-cultured for 6 days and then, cell division was evaluated by flow cytometry.

6. On day 6 of the co-culture, cell division was evaluated by flow cytometry. Results are shown in FIG. 3. The upper images show the results obtained with the T cells (effector cells) derived from donor A and the lower images show the results obtained with the T cells derived from donor B.

7. FIG. 4 shows the ratio of the cell proliferation induced by the specific MLR. The CD8 positive T cells re-generated from the iPS cells with a homozygous HLA haplotype did not exert the MLR reaction against the cells from donor A having HLA haplotypes one of which matched the iPS cells' HLA. On the other hand, the T cells exerted the MLR reaction against the T cells of donor B having HLA haplotypes that did not match the iPS cells' HLA haplotype at all.

Based on the above results, CD8 positive T cells re-generated from iPS cells with a homozygous HLA haplotype do not activate the T cells having heterologous HLA haplotypes one of which matches the iPS cells. Accordingly, CTLs re-generated from iPS cells with a homozygous HLA haplotype do not exert graft-versus-host-disease against a subject who has heterozygous HLA haplotypes one of which matches the iPS cells and therefore, the cell-based immunotherapy can be conducted effectively with those CTLs.

EXAMPLE 3

T-iPS cells with a homozygous HLA haplotype obtained in Example 1 were differentiated into CD8 positive T cells (CTLs) by a conventional procedure. Whether or not the CTL activated the NK cells derived from peripheral blood of a subject with heterozygous HLA haplotypes one of which matched the HLA haplotype of the T-iPS cells was examined.

1. CD8 positive T cells differentiated by a conventional procedure from the iPS cells with a homozygous HLA haplotype obtained in Example 1 were used as stimulators.

2. iPS cells were established by a conventional procedure from a cell of donor A having heterozygous HLA haplotypes one of which matched the HLA haplotype of the stimulator cells, and the obtained iPS cells were differentiated into CD8 positive T cell by a conventional procedure. Thus obtained CD8 positive T cells were also used as stimulators.

3. Peripheral blood of donor A was obtained and peripheral blood mononuclear cells (PBMCs) were isolated by using Ficoll. NK cells were enriched from the PBMCs by means negative selection with CD3, CD4, CD8, CD14 and CD19 microbeads. Thus obtained NK cells were used as effectors.

4. The stimulators, i.e. the re-generated CD8 positive T cells and effectors, i.e. the NK cells were mixed so that the effector/stimulator cell ratio was 1:1 ($1\times10^5$ cells each) and the cells were co-cultured for 6 hours in a medium supplemented with IL-2 (1000 U/mL) and anti-CD107a antibody.

Figure 5:
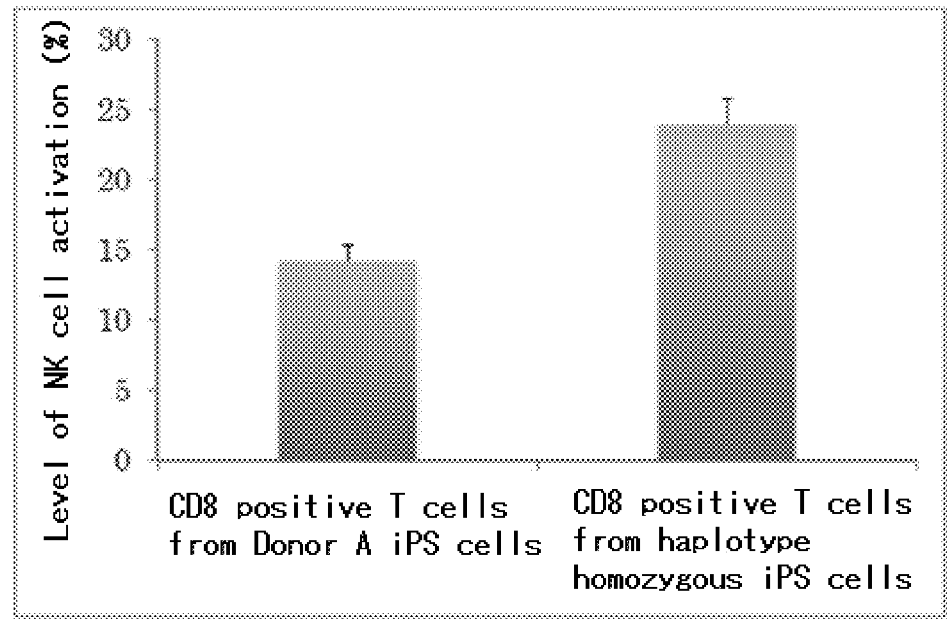
FIG. 5 shows that CD8 positive T cells induced from iPS cells with a homozygous HLA haplotype activated NK cells with heterozygous HLA haplotypes one of which matched the iPS cells' HLA haplotype.

5. After 6 hours of co-culture, activation of the NK cells was evaluated by flow cytometry. The results are shown in FIG. 5.

6. The CD8 positive T cells differentiated from iPS cells established from cells of donor A did not activate the NK cells derived from donor A. On the other hand, CD8 positive T cells differentiated from iPS cells with a homozygous HLA haplotype activated NK cells derived from donor A one of whose HLA haplotypes matched the homozygous HLA haplotype.

7. Based on the above results, the inventors have concluded as follows.

CD8 positive T cells differentiated from iPS cells with a homozygous HLA haplotype activated NK cells having heterozygous HLA haplotypes one of which matched the homozygous HLA haplotype. Accordingly, when mature T cells or CTLs re-generated from iPS cells with a homozygous HLA haplotype are transplanted in a recipient having heterozygous HLA haplotypes one of which matches the donor's HLA haplotype, the transplanted T cells will gradually be eliminated by the function of the NK cells. Therefore, the T cells obtained by the method of this application can be used for safe treatment with significantly less risk of canceration of the transplanted cells.

According to the result of Example 2, recipient's T cells do not fight against T cells re-generated from iPS cells established from a cell of a donor who has a homozygous HLA haplotype, when recipient has at least one HLA haplotype that matches the HLA haplotype of the donor. Transplantation from a donor with a homozygous HLA haplotype to a recipient having heterozygous HLA haplotypes one of which matches the homozygous HLA haplotype (allograft) will be advantageous when the cells to be transplanted are lymphocytes than when the re-generated cells are the other nucleated cells. According to Example 3, upon transplantation from a donor having a homozygous HLA haplotype to a recipient having heterozygous HLA haplotypes, NK cells will reject the cells from the donor. By this mechanism, the transplanted lymphocytes are eventually rejected and therefore, the method can avoid the risk that the transplanted lymphocytes become cancer.

EXAMPLE 4

T-iPS cells were established from a T cell specific for LMP2 antigen derived from peripheral blood mononuclear cells of an EB virus carrier. T-iPS cells were differentiated into LMP2 antigen specific CTLs.

EB virus infection in acute phase may cause infectious mononucleosis and sometimes cause cancer such as barkitt lymphoma. In this example, the donor for T cells was a healthy person who had previously been infected with EB virus. Once infected, this virus stays in the lymphocytes for entire life and therefore, the donor is an EB virus carrier. The donor is, therefore, considered to have chronic EB virus infection.

1) Propagation of Cytotoxic T Lymphocytes (CTL) Specific for LMP2 Antigen i) The following media were used.

Medium for Dendritic Cells: CellGro (CellGenix)

TABLE 4

| Medium for T cells (T cell medium): | | |
|---|---|---|
| | Amount | Final conc. |
| RPMI | 45 ml | |
| human AB serum | 5 ml | 10% |
| Total | 50 ml | |

ii) The LMP2 antigen peptide used is as follows.

LMP2: IYVLVMLVL (SEQ ID NO: 1)

LMP2 tetramer was purchased from MBL.

iii) The LCL (Lymphoblastoid cell line) used is as follows.

Lymphoblastoid cell line (LCL) having HLA-A2402 established from a healthy volunteer who had previously infected with EB virus in the Department of Hematology and Oncology, Graduate School of Medicine, Kyoto University, Kyoto, Japan was used.

A. Induction of Human Monocyte-Derived Dendritic Cells (MoDC) from Human Peripheral Blood 1. Peripheral blood was obtained from healthy volunteer A having HLA-A2402 who had previously been infected with EB virus. Monocytes were isolated from the blood by using CD14 microbeads. The cells were washed and added with the medium for dendritic cells to give a $5\times10^5$ cells/mL suspension.

2. Cytokines were added to the cell suspension to give final concentrations of GM-CSF 800 U/mL (or 50 ng/mL), IL-4 200 U/mL (or 40 ng/mL). Five milliliter (5 mL) of the cell suspension was seeded on each well of a 6-well plate. The plate was incubated at 37° C. with 5% $CO_2$.

3. The plate was incubated for 3 days and on day 3, 2.5 mL of the culture supernatant was gently removed. Fresh medium for dendritic cells were added with GM-CSF and IL-4 to give final concentrations of 800 U/mL and 200 U/mL respectively.

4. Thus prepared fresh medium for dendritic cells 3 mL was added to each well.

5. On day 6, immature monocyte-derived dendritic cells (MoDCs) were collected from the plate and added in a small amount of fresh medium for dendritic cells.

6. The density of the cell suspension was adjusted to $5\times10^5$ cells/mL.

7. GM-CSF (final concentration: 800 U/mL), IL-4 (final concentration: 200 U/mL), TNF-alpha (final concentration: 10 ng/mL), and PGE2 (final concentration: 1 μg/mL) were added to the cell suspension. About $5\times10^5$ cells/mL/well of the cell suspension was added to each well of a 24-well plate.

8. The plate was incubated at 37° C. with 5% CO2 for 24 hours.

9. The peptide was added to each well in last 2 hours of the 24 hours incubation period. The final concentration of the peptide was 10 μM. Dendritic cells (DC) were collected from the plate and washed twice with the medium for T cells.

10. The number of the DCs was counted and the medium for T cells was added to give a $2\times10^5$ cells/mL suspension.

B. Isolation of T Cells from Human Peripheral Blood and Co-Culture of the T Cells and Dendritic Cells.

1. T cells were isolated from peripheral blood of the healthy volunteer A (the same person in the step A above) by means of the MACS technique using CD3 microbeads. The cells were washed and added with the medium for T cells to give a $2\times10^6$ cells/mL suspension. A small part of the T cell suspension was separated for the flow cytometry analysis.

2. 0.5 mL/well of DC cell suspension ($2\times10^5$ cells/mL) and 0.5 mL/well of the T cell suspension ($2\times10^6$ cells/mL) were added together to each well of a 24 well plate. (DC cells: T cells=$1\times10^5$: $1\times10^{6=}$1:10).

3. On day 3, IL-7 (final concentration: 5 ng/mL) and IL-15(final concentration: 10 ng/mL) were added to each well.

4. On day 14, the cells were collected from the culture.

C. Addition of the Peptide to LCL

1. LCLs were collected from the culture and irradiated at a dose of 35 Gy.

2. The irradiated cells were suspended in the T cell medium to give a $5\times10^5$ cells/mL suspension.

3. The peptide was added to the suspension 100 nM and incubated for 2 hours.

4. The LCL were collected and washed with the T cell medium and then, dispersed in the T cell medium to give a $2\times10^5$ cells/mL suspension.

D. Co-Culture of LCL and T Cells Stimulated with the Dendritic Cells.

1. The T cells stimulated with the dendritic cells were dispersed in the T cell medium to give a $2\times10^6$ cells/mL suspension.

2. 0.5 mL/well of the LCL suspension ($2\times10^5$ cells/mL) incubated in the presence of the peptide and 0.5 mL/well of T cell suspension ($2\times10^6$ cells/mL) were added together to each well of a 24-well plate (LCL: T cells=$1\times10^5$:$1\times10^6$=1: 10). Simultaneously, the peptide was added to the well to give the final concentration of 100 nM.

3. On day 3, IL-7 (final concentration: 5 ng/mL) and IL-15 (final concentration: 1 ng/mL) were added to the well. The plate was incubated for 2 weeks and the medium was changed every week with the fresh T cell medium supplemented with the cytokines. (1st course of stimulation with peptide-pulsed LCL)

4. LCLs were again incubated in the medium supplemented with 100 nM of the peptide for 2 hours and then, added with the CTLs.

5. On day 3, IL-7 (final concentration: 5 ng/mL) and IL-15 (final concentration: 1 ng/mL) were added to the well. The plate was incubated for 2 weeks and the medium was changed every week with the fresh T cell medium supplemented with the cytokines. (2nd course of stimulation with peptide-pulsed LCL)

Figure 6:
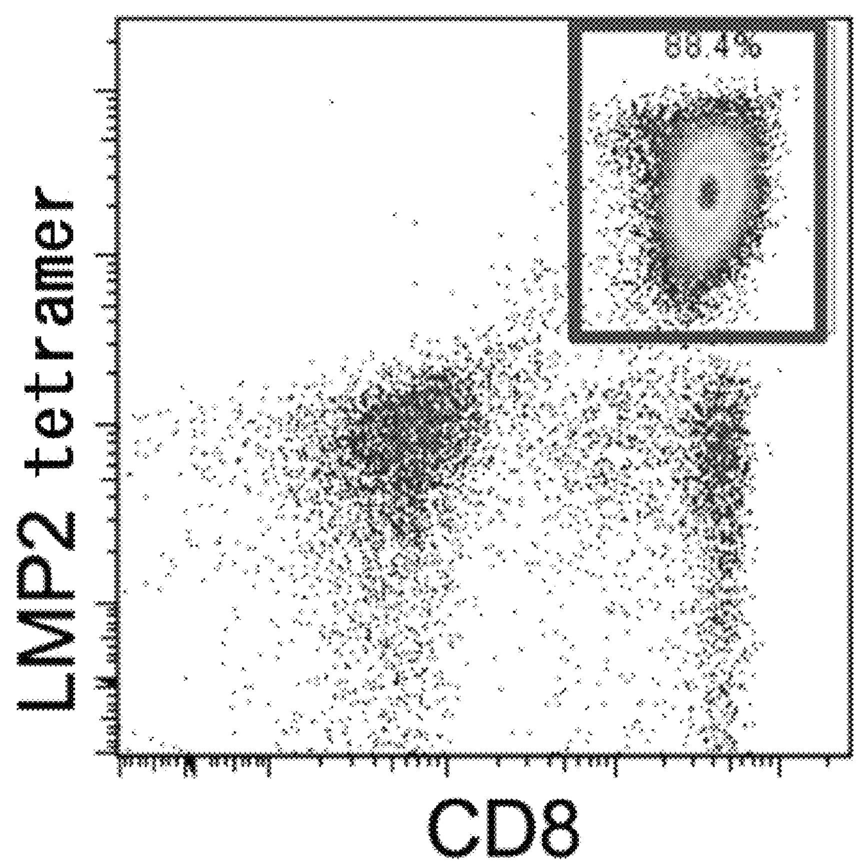
FIG. 6 is a result of FACS analysis showing that LMP2 tetramer positive-CD8 positive T cells were induced from T cells of a healthy volunteer in example 4.

6. Thus obtained cells were analyzed by flow cytometry and confirmed that more than 80% of CD8 positive T cells were CD8 positive and LMP-2 tetramer positive cells. Results are shown in FIG. 6.

E. Antigen Specific Killer Activity of the LMP2 Specific CTLs

1. CFSE-labelled OUN-1 leukemia cells were used as target cells. The labelled cells were dispersed in the T cell medium and incubated in the presence of 1 nM of the LMP2 peptide for 2 hours.

Figure 7:
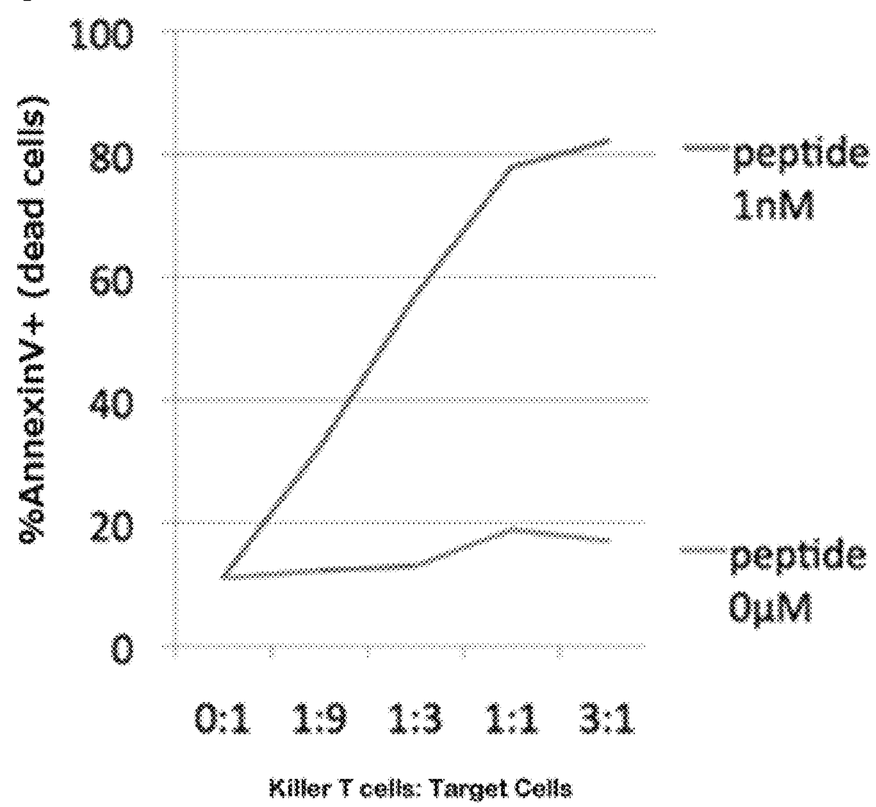
FIG. 7 shows that T cells induced by using LMP2 peptide from peripheral blood obtained from a healthy volunteer having HLA-A2402 who had previously been infected with EB virus exerted the peptide specific killer activity in example 4.

2. LMP2 specific cytotoxic T cells (CD8 positive and LMP-2 tetramer positive cells) expanded under the peptide stimulation and the CFSE-labelled OUN-1 leukemia cells were added together to each well of a 96-well round bottom plate at different effector/target cell ratios of 0:1, 1:9, 1:3, 1:1 and 3:1. The cells were incubated in the presence or absence of the peptide. The ratio of Annexin V positive cells to PI (Propidium Iodide) positive cells in the CFSE positive cell fraction were determined to confirm percentage of dead cells among the target cells. Results are shown in FIG. 7.

3. Thus prepared LMP2 specific killer T cells were confirmed to have the antigen specific killer activity against the target cells.

b) Establishment of the LMP2-T-iPS Cells

A. Activation of LMP2 specific CTLs.

1. CD8 positive cells were enriched from the above obtained LMP2 specific CTLs by using MACS beads.

2. The enriched cell population was dispersed in the T cell medium and added with IL-7 (final concentration: 5 ng/mL) and IL-15 (final concentration: 10 ng/mL). Dynabeads Human T-Activator CD3/CD28 was added to give a bead-to-cell ratio of 1:1, and the mixture was incubated for 2 days to activate the CD8 positive cells.

B. Introduction of the Yamanaka Four Factors and SV40 by means of Sendai Virus Vector.

1. The activated LMP2 specific CTLs were dispersed in the T cell medium, Sendai virus bearing four Yamanaka factors and SV40 was added to the medium and the cell suspension was cultured for 2 days.

2. The obtained cells were washed with the T cell medium and added with the T cell medium supplemented with IL-7 (final concentration: 5 ng/mL) and IL-15 (final concentration: 1 ng/mL). The cells were further cultured for 2 days.

3. After that, all cells were collected and dispersed in the T cell medium supplemented with IL-7 (final concentration:

5 ng/mL) and IL-15 (final concentration: 1 ng/mL). The cell suspension was seeded on the feeder cells.

4. On day 2, a half of the medium was replaced with the fresh iPS cell medium. After that, a half of the medium was replaced with fresh iPS cell medium every day and the cells were continuously cultured.

C. Picking up iPS Cell Colonies from the Culture

1. Three weeks after the introduction of the Yamanaka factors, colonies of iPS cells were visually observed.

2. Colonies were mechanically picked up with a 200 μl pipette tip.

Figure 8:
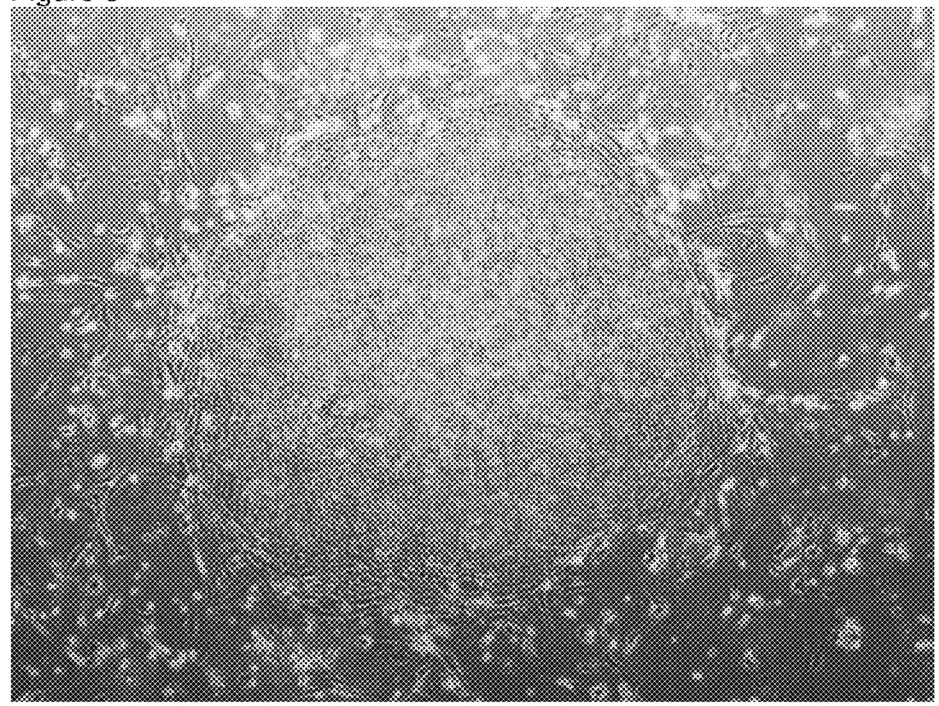
FIG. 8 is a photograph of an iPS cell colony induced from a LMP2 peptide specific T cell.

3. Several clones were established individually and one of them was used as LMP2-T-iPS cells in the example below. Photograph of the colony of an obtained clone is shown in FIG. 8.

3) Induction of T Cells from the LMP2-iPS Cells. Media used are as Follows:

TABLE 5

| Medium A: for maintenance of OP9 stromal cells | | |
|---|---|---|
| contents | amount added | final conc. |
| αMEM medium | 500 mL | |
| FCS | 125 mL | 20% |
| penicillin-streptomycin solution* | 6.25 mL | 1% |
| Total | 631.25 mL | |

*Mixture of Penicillin (10,000 U/ml) and Streptomycin (10,000 μg/ml). The final concentrations were 100 U/ml and 100 μg/ml, respectively.

TABLE 6

| Medium B: for inducing differentiation of T cells | | |
|---|---|---|
| contents | amount added | final conc. |
| αMEM medium | 500 mL | |
| FCS | 125 mL | 20% |
| penicillin-streptomycin solution* | 5 mL | 1% |
| hrIL-7 (stock: 10 μg/mL) | 315 μL | 5 ng/mL |
| hrFlT-3L (stock: 10 μg/mL) | 315 μL | 5 ng/mL |
| hrSCF (stock: 10 μg/mL) | 630 μL | 10 ng/mL |
| Total | 631.26 mL | |

*Mixture of Penicillin (10,000 U/ml) and Streptomycin (10,000 μg/ml). The final concentrations were 100 U/ml and 100 μg/ml, respectively.

TABLE 7

| Medium C: for inducing from immature T cells into mature T cells | | |
|---|---|---|
| contents | amount added | final conc. |
| αMEM medium | 500 mL | |
| FCS | 125 mL | 20% |
| penicillin-streptomycin solution* | 5 mL | 1% |
| hrIL-7 (stock: 10 μg/mL) | 315 μL | 5 ng/mL |
| Total | 630.315 mL | |

*Mixture of Penicillin (10,000 U/ml) and Streptomycin (10,000 μg/ml). The final concentrations were 100 U/ml and 100 μg/ml, respectively.

Preparation of OP9 Cells

Six milliliters (6 mL) of 0.1% gelatin solution in PBS was added to a 10 cm dish (Falcon) and incubated for 30 minutes at 37° C. The gelatin solution was then removed and 10 mL of medium A was added to the dish. About ¼ of the OP9 stromal cells in a confluent culture were obtained and seeded on the dish. Four days after, 10 mL of fresh medium A was added to the dish (final amount was 20 mL).

Induction of Hematopoietic Progenitor Cells from iPS Cells

The medium in the OP9 stromal cell culture to be used for the co-culture was aspirated and replaced with fresh medium A. The medium in the iPS cell culture dish was also aspirated and 10 ml of fresh medium A was added. The iPS cell mass was cut with an EZ-passage roller. The cut iPS cell mass was suspended by using a pipetman with a 200 μl tip. The number of the iPS cell clusters was visually counted and approximately 600 iPS cell clusters were seeded on the OP9 cells. Three or more dishes per clone of iPS cells were used, and when subculturing, the cells in all dishes were once pooled in one dish and then redistributed to the same number of dishes to reduce the disparity between the dishes.

Day 1: (the Medium was Replaced)

Whether or not the iPS cell mass adhered to the dish and started to differentiate were confirmed. The cell culture medium was replaced with 20 mL of fresh medium A.

Day 5: (a Half of the Medium was Replaced)

A half of the cell culture medium was replaced with 10 mL of fresh medium A.

Day 9: (a Half of the Medium was Replaced)

A half of the cell culture medium was replaced with 10 mL of fresh medium A.

Day 13: (Induced Mesodermal Cells were Transferred from OP9 Cell Layer onto OP9/DLL1 Cell Layer)

Cell culture medium was aspirated to remove and the surface of the cultured cells were washed with HBSS(+Mg+Ca) to washout the cell culture medium. 10 mL of Collagenase IV 250U in HBSS (+Mg+Ca) solution was added to the dish and incubated for 45 minutes at 37° C.

The collagenase solution was removed by aspiration and the cells were washed with 10 mL of PBS(−). Then, 0.05% trypsin/EDTA solution was added to the dish and the dish was incubated for 20 minutes at 37° C. After the incubation, the sheet like cell aggregates peeled from the bottom of the dish and the cell aggregates were mechanically fragmented to smaller sizes by means of pipetting. Thus treated cells were added with fresh medium A 20 mL and cultured for another 45 minutes at 37° C.

The culture medium containing the floating cells was passed through 100 μm mesh and the cells were collected. The cells were then centrifuged at 1200 rpm for 7 minutes at 4° C. The obtained pellet was suspended in 10 mL of medium B. One-tenth of the suspension was separated and used for the FACS analysis. The remaining cell suspension was seeded on new dishes containing OP9/DLL1 cells. Cell suspensions obtained from several dishes were pooled and the pooled cells were seeded on the same number of new dishes.

Figure 9:
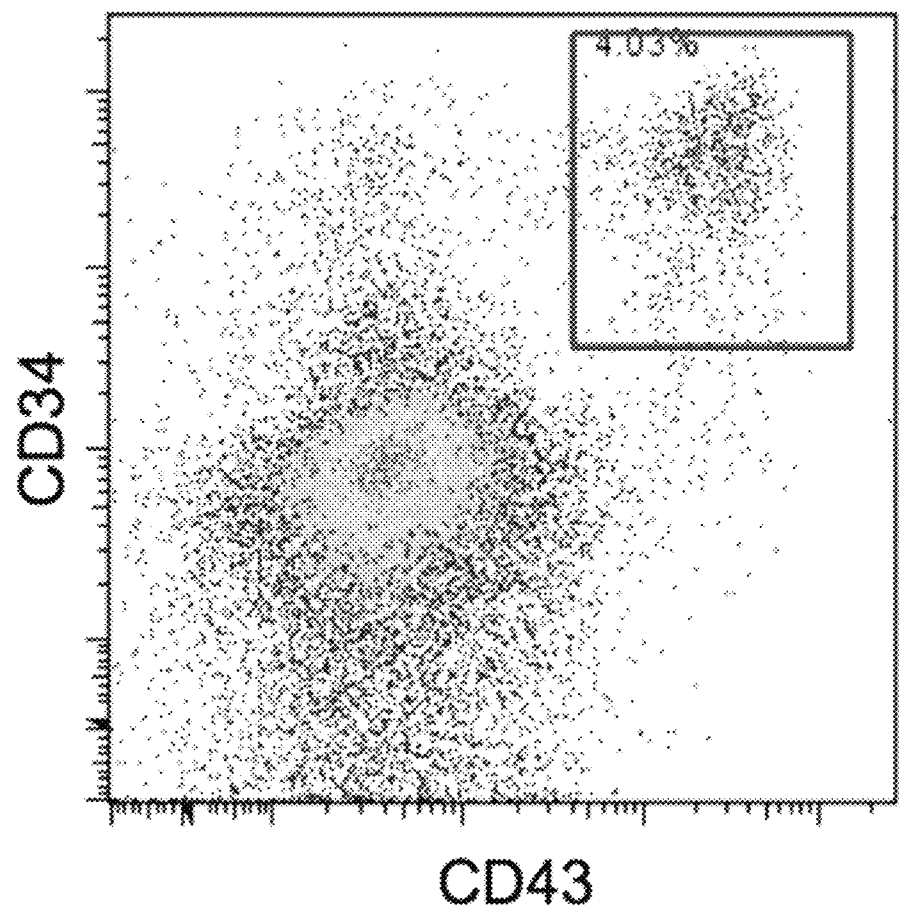
FIG. 9 is a result of FACS analysis of the cells on day 13 of the differentiation of T-iPS cells established from LMP2 peptide specific T cells into T cells.

In order to ascertain whether or not hematopoietic progenitor cells were contained in the obtained cells, FACS analysis was carried out using anti-CD34 antibody and anti-CD43 antibody. The results are shown in FIG. 9. Since a sufficient number of cells could be confirmed in the $CD34^{low}CD43^{+}$ cell fraction, it was confirmed that hematopoietic progenitor cells were induced.

C. Induction of T Cells from Hematopoietic Progenitor Cells.

Then, the obtained cells were seeded on OP9/DLL1 cells. In this step, cell sorting of the $CD34^{low}CD43^{+}$ cell fraction was not performed. When this fraction is sorted, the efficiency of differentiation of T cells could be reduced in comparison with the case where sorting was not performed due to the decrease of the cells or damage to the cells by sorting.

During the culturing period, FACS analysis was conducted several times to confirm the differentiation stages. A considerable number of dead cells were observed over the culturing period. Before the FACS analysis, dead cells were eliminated by using, for example, Propidium Iodide (PI) or 7-AAD.

Day 16: (Cells were Subcultured)

The cells loosely adhered to the OP9 cells were dissociated by gently pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cell suspension was seeded on new dishes containing OP9/DLL1 cells.

Day 23: (Cells were Subcultured) Blood Cell Colonies began to appear.

The cells loosely adhered to the OP9/DLL1 cells were dissociated by gently pipetting several times. The cells were passed through a 100 μm mesh and collected in a 50 mL conical tube. The tube was centrifuged at 1200 rpm for 7 minutes at 4° C. The pellet was dispersed in 10 mL of medium B.

Day 36: LMP2 Tetramer Positive Cells were Confirmed

In order to confirm T cells specific for the LMP2 antigen were induced, the cells on Day 36 were analyzed by FACS with anti CD3 antibody and LMP2 tetramer.

Figure 10:
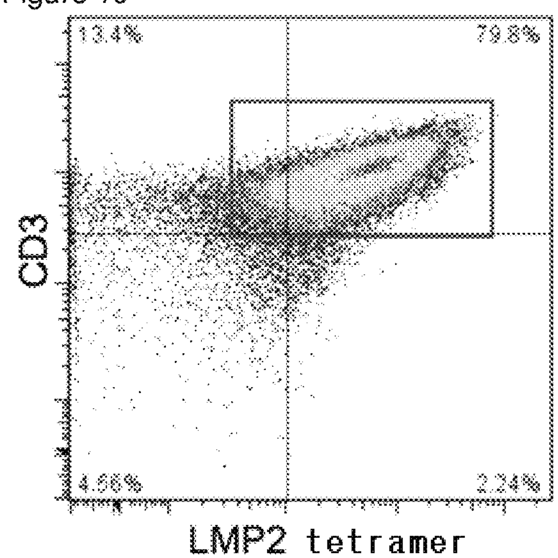
FIG. 10 is a result of FACS analysis of the cells on day 36 of the differentiation of T-iPS cells established from LMP2 peptide specific T cells into T cells.

Results are shown in FIG. 10. $CD3^+$ cells were observed and a part of the cells were differentiated into $CD3^+$LMP2 tetramer positive cells.

D. Induction of Mature Killer T Cells from the Immature T Cells.

On day 36, LMP2 positive T cells were confirmed with flow cytometry and then, the cells were added with IL-15 so that the cells are differentiated into mature killer T cells or CD8SP cells. The T cells were dispersed in medium C and seeded on the fresh OP9/DLL1 cell layer in each well of a 24-well plate at a density of $3\times10^5$ cells/well. IL-15 was added to each well to give final concentration of 10 ng/mL.

Day 41: Mature Killer T Cells Were Observed

Figure 11:
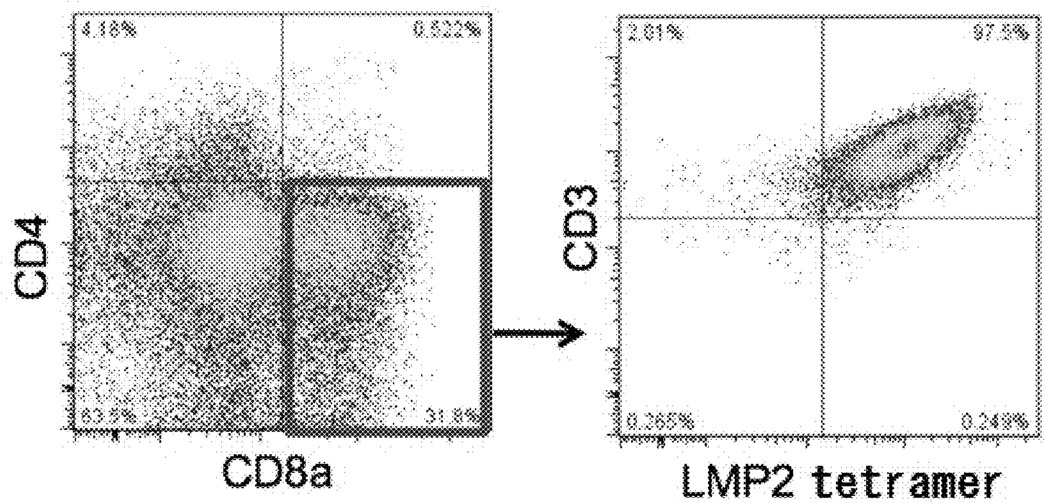
FIG. 11 is a result of FACS analysis of the cells on day 41 of the differentiation of T-iPS cells established from LMP2 peptide specific T cells into T cells. Generation of LMP2 specific mature T cells (CTLs) was confirmed.

Five days after the addition of IL-15, the cells were analyzed with FACS. Result is shown in FIG. 11. Mature CD8 single positive cells were observed.

4) Antigen-Specific Killer Activity of the Re-Generated LMP2 Specific CTLs

1. CFSE-labelled LCLs were used as target cells. The labelled cells were dispersed in the T cell medium and incubated in the presence of 1 nM of the LMP2 peptide for 2 hours.

2. The re-generated CD8 single positive T cells and the target cells (LCLs) were added together to each well of a 96-well round bottom plate at different effector/target cell ratios of 0:1, 1:9, 1:3, 1:1, 3:1, 10:1 and 30:1. The cells were incubated in the presence (p+) or absence (p−) of the peptide. The ratio of Annexin V positive cells to PI (Propidium Iodide) positive cells in the CFSE positive cell fraction were determined to confirm percentage of dead cells among the target cells.

Figure 12:
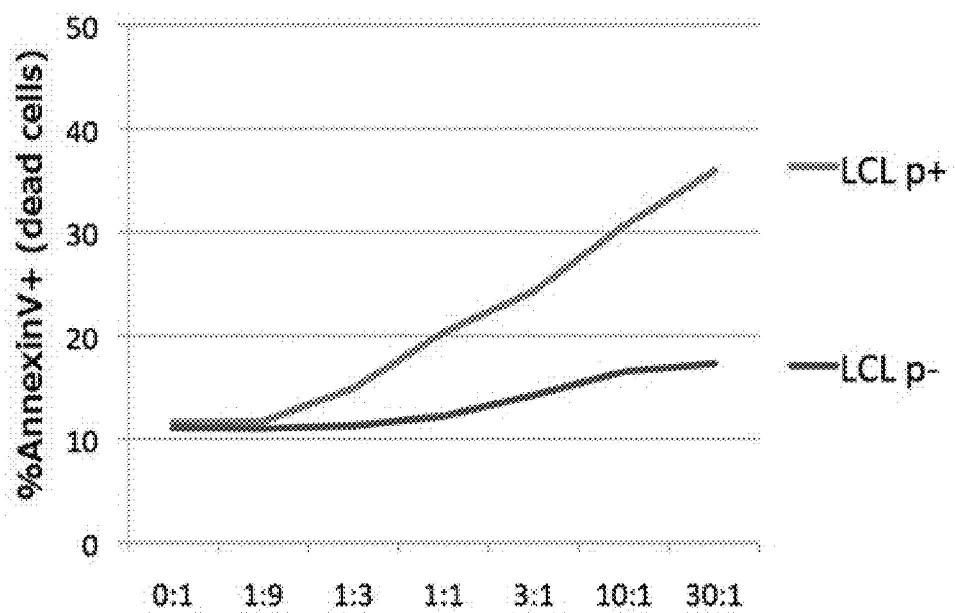
FIG. 12 shows LMP2 specific killer activity of the mature T cells (CTLs) re-generated from T-iPS cells established from a LMP2 peptide specific T cell. The killer activities in the presence (p+) or absence (p−) of LMP2 peptide were observed by using LCLs as target cells.

3. Results are shown in FIG. 12. Thus prepared LMP2 specific killer T cells were confirmed to have the antigen specific killer activity against the target cells.

5) Natural Killer Cell-Like Activity of the Re-Generated LMP2 Specific CTLs

1. K562 cell line that does not express HLA on the cell surface (to determine alloreactivity) and autologous peripheral mononuclear cells (MA p−) (to determine auto reactivity) were used as target cells. Those cells were labelled with CFSE and suspended in the T cell medium.

2. The re-generated CD8T cells and the target cells were added together to each well of a 96-well round bottom plate at different effector/target cell ratios of 0:1, 1:9, 1:3, 1:1, and 3:1. The cells were incubated and the ratio of Annexin V positive cells to PI (Propidium Iodide) positive cells in the CFSE positive cell fraction were determined to confirm percentage of dead cells among the target cells.

Figure 13:
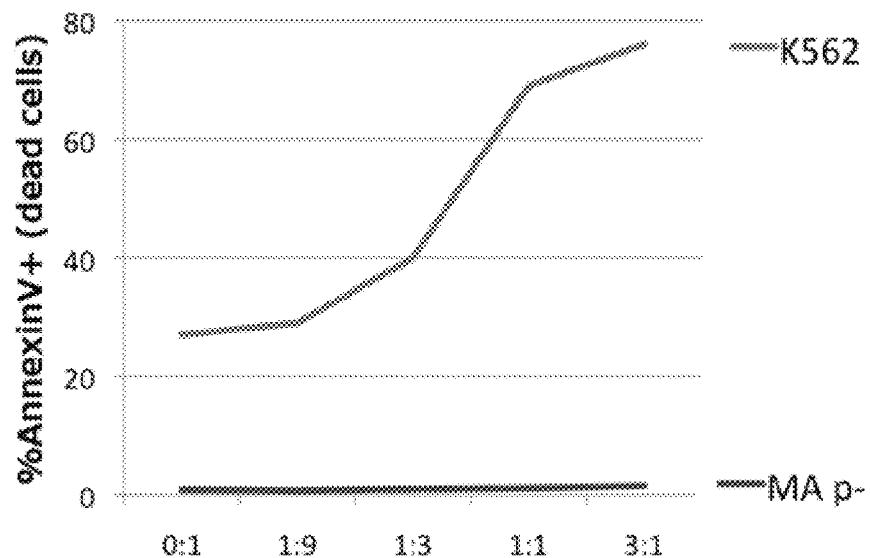
FIG. 13 shows natural killer cell-like activities of mature T cells re-generated from T-iPS cells established from a LMP2 peptide specific T cell.

3. Results are shown in FIG. 13. The LMP2 specific killer T cells did not kill the autologous PBMC (MA p−) but showed high killer activity against K562 cells. This result support that the LMP2 specific killer T cells have natural-killer cell like activity.

EXAMPLE 5

WT1 antigen specific cytotoxic T cells were induced from peripheral blood of a healthy volunteer, and T-iPS cells were established from the CTL. Then, WT1 antigen specific mature T cells were induced from the T-iPS cells.

This example comprises the following steps:

1) Amplification of WT1 antigen specific CTLs
2) Establish of WT1-T-iPS cells
3) Induction T cells from the WT1-T-iPS cells.

1) Amplification of WT1 antigen specific CTL i) The medium used is as follows.

TABLE 8

| Medium for T cells (T cell medium): | | |
|---|---|---|
| | Amount | Final conc. |
| RPMI | 45 ml | |
| human AB serum | 5 ml | 10% |
| Total | 50 ml | |

ii) The WT1 antigen peptide used is as follows.

WT1 modified form: CYTWNQMNL (SEQ ID NO: 2) Cancer Immunol. Immunothera. 51:614 (2002))

Both WT1 peptide and WT1 tetramer used below were the modified form.

iii) The LCL (Lymphoblastoid cell line) used is as follows.

The LCL having HLA-A2402 which had been established from a healthy volunteer in the Department of Hematology and Oncology, Graduate School of Medicine, Kyoto University, Kyoto, Japan was used.

A. Isolation of T Cells from Human Peripheral Blood and Stimulation of the Cells with the Peptide 1. Peripheral blood was obtained from a healthy volunteer. Monocytes were purified from the blood by using Ficoll and dispersed in the T cell medium.

2. The cell suspension was added to each well of a 96-well round bottom plate in a density of $2.5\times10^5$ cells/mL/well, and the peptide was added to give the final concentrations of 10 μM.

3. On day 3, IL-2 (final concentration: 12.5 U/mL), IL-7 (final concentration: 5 ng/mL) and IL-15 (final concentration: 1 ng/mL) were added to the well. The plate was incubated for 2 weeks and the medium was changed every week with the fresh T cell medium supplemented with the cytokines.

B. Addition of the Peptide to LCLs.

1. LCLs were collected from the culture and irradiated at a dose of 35Gy.

2. The irradiated cells were suspended in the T cell medium to give a $5\times10^5$ cells/mL suspension.

3. The peptide 100 nM was added to the suspension and incubated for 2 hours.

4. The LCLs were collected and washed with the T cell medium and then, dispersed in the T cell medium to give a $2\times10^5$ cells/mL suspension.

C. Co-Culture of LCL Pulsed with the Peptide and T Cells.

1. The peptide stimulated T cells were collected when they were incubated for two weeks after the peptide stimulation, washed and then dispersed in the T cell medium to give $2\times10^6$ cells/mL suspension. A small part of the T cell suspension was separated for the flow cytometry analysis.

2. A LCL suspension ($2\times10^5$ cells/mL) that had been incubated in the presence of the peptide 0.5 mL/well and the T cell suspension ($2\times10^6$ cells/mL) 0.5 mL/well were added together to each well of a 24 well plate. (LCLs: T cells=$1\times10^5:1\times10^6$=1:10).

3. On day 3, IL-2 (final concentration: 12.5 U/mL), IL-7 (final concentration: 5 ng/mL) and IL-15 (final concentration: 1 ng/mL) were added to each well. The plate was incubated for 2 weeks and the medium was changed every week with the fresh T cell medium supplemented with the cytokines. (1st course of stimulation with peptide-pulsed LCL)

4. LCLs were again incubated in the medium supplemented with 100 nM of the peptide for 2 hours and then, added with the CTLs.

5. On day 3, IL-2 (final concentration: 12.5 U/mL), IL-7 (final concentration: 5 ng/mL) and IL-15 (final concentration: 1 ng/mL) were added to each well. The plate was incubated for 2 weeks and the medium was changed every week with the fresh T cell medium supplemented with the cytokines. (2nd course of stimulation with peptide-pulsed LCL)

6. LCLs were again incubated in the medium supplemented with 100 nM of the peptide for 2 hours and then, added with the CTLs.

7. On day 3, IL-2 (final concentration: 12.5 U/mL), IL-7 (final concentration: 5 ng/mL) and IL-15 (final concentration: 1 ng/mL) were added to each well. The plate was incubated for 2 weeks and the medium was changed every week with the fresh T cell medium supplemented with the cytokines. (3rd course of stimulation with peptide-pulsed LCL)

Figure 14:
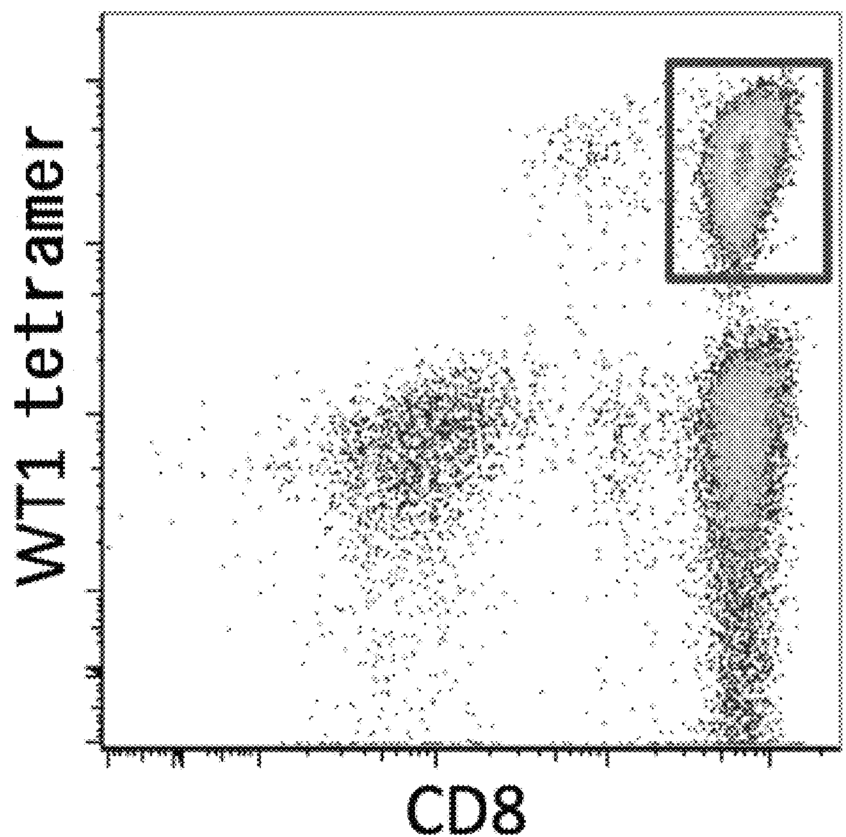
FIG. 14 is a result of FACS analysis that shows WT1 tetramer positive and CD8 positive cells were induced from T-iPS cells established from a cell of a donor with a homozygous HLA haplotype in Example 5.

8. Thus obtained cells were analyzed by flow cytometry. The result is shown in FIG. 14. It was confirmed that more than 60% of the CD8 positive T cells were CD8 positive and WT1 tetramer positive cells.

2) Establish of the WT1-T-iPS Cells

A. Activation of WT1 Specific CTLs.

1. CD8 positive cells were enriched from the above obtained WT1 specific CTLs using MACS beads.

2. The enriched cell population was dispersed in the T cell medium and added with IL-2 (final concentration: 12.5 U/mL), IL-7 (final concentration: 5 ng/mL) and IL-15 (final concentration: 1 ng/mL). Dynabeads Human T-Activator CD3/CD28 was added to give a bead-to-cell ratio of 1:1, and the mixture was incubated for 2 days to activate the CD8 positive cells.

B. Introduction of the Yamanaka Four Factors and SV40 by means of Sendai Virus Vector.

1. The activated WT1 specific CTLs were dispersed in the T cell medium, Sendai virus bearing four Yamanaka factors and SV40 was added to the medium and the cell suspension was cultured for 2 days.

2. The obtained cells were washed with the T cell medium and added with the T cell medium supplemented with IL-2 (final concentration: 12.5 U/mL), IL-7 (final concentration: 5 ng/mL) and IL-15 (final concentration: 1 ng/mL). The cells were further cultured for 2 days.

3. After that, all cells were collected and dispersed in the T cell medium containing no cytokine. The cell suspension was seeded on the feeder cells.

4. On day 2, a half of the medium was replaced with the fresh iPS cell medium. After that, a half of the medium was replaced with the fresh iPS cell medium every day and the cells were continuously cultured.

C. Picking up iPS Cell Colonies from the Culture

1. Three weeks after the introduction of the Yamanaka factors, colonies of iPS cells were visually observed.

2. Colonies were mechanically picked up with a 200 µl pipette tip.

Figure 15:
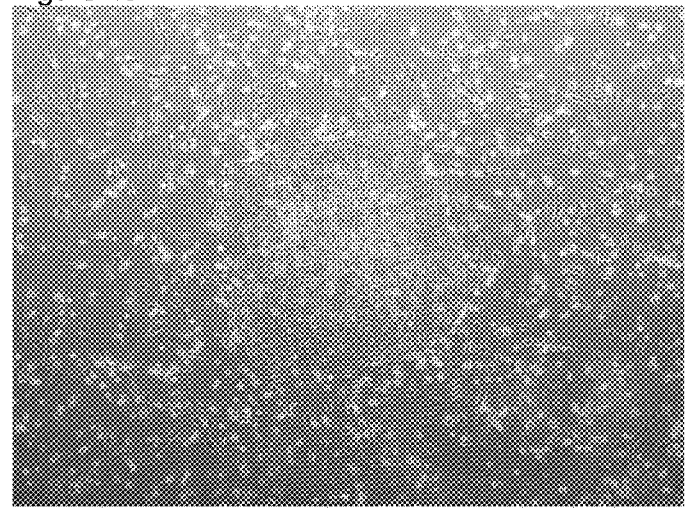
FIG. 15 is a photograph of an iPS cell colony established from a WT1 peptide specific T cell.

3. Several clones were established individually. Photograph of the colony of an obtained clone is shown in FIG. 15.

3) Induction of T cells from the WT1-T-iPS Cells.

Media used are as follows:

TABLE 9

Medium A: for maintenance of OP9 stromal cells

| contents | amount added | final conc. |
|---|---|---|
| αMEM medium | 500 mL | |
| FCS | 125 mL | 20% |
| penicillin-streptomycin solution* | 6.25 mL | 1% |
| Total | 631.25 mL | |

*Mixture of Penicillin (10,000 U/ml) and Streptomycin (10,000 µg/ml). The final concentrations were 100 U/ml and 100 µg/ml, respectively.

TABLE 10

Medium B: for inducing differentiation of T cells

| contents | amount added | final conc. |
|---|---|---|
| αMEM medium | 500 mL | |
| FCS | 125 mL | 20% |
| penicillin-streptomycin solution* | 5 mL | 1% |
| hrIL-7 (stock: 10 µg/mL) | 315 µL | 5 ng/mL |
| hrFlT-3L (stock: 10 µg/mL) | 315 µL | 5 ng/mL |
| hrSCF (stock: 10 µg/mL) | 630 µL | 10 ng/mL |
| Total | 631.26 mL | |

*Mixture of Penicillin (10,000 U/ml) and Streptomycin (10,000 µg/ml). The final concentrations were 100 U/ml and 100 µg/ml, respectively.

Preparation of OP9 Cells

Six milliliters (6 mL) of 0.1% gelatin solution in PBS was added to a 10 cm dish (Falcon) and incubated for 30 minutes at 37° C. OP9 stromal cells were detached from a confluent culture dish with trypsin/EDTA solution and about ¼ of the obtained cells were added to the gelatin coated 10 cm cell culture dish. 10 mL of medium A was added to the cell culture dish. Four days after, medium A 10 mL was added to the dish (final amount was 20 mL).

Induction of Hematopoietic Progenitor Cells from iPS Cells

The medium in the OP9 stromal cell culture to be used for the co-culture was aspirated and replaced with fresh medium A. The medium in the iPS cell culture dish was also aspirated and 10 ml of fresh medium A was added. The iPS cell mass was cut with an EZ-passage roller. The cut iPS cell mass was suspended by means of a pipetman with a 200 µl tip. The number of the iPS cell clusters was visually counted and approximately 600 iPS cell clusters were seeded on the OP 9 cells. Three or more dishes per clone of iPS cells were used, and when subculturing, the cells in all dishes were once pooled in one dish and then redistributed to the same number of dishes to reduce the disparity between the dishes.

Day 1: (the Medium was Replaced)

Whether or not the iPS cell mass adhered to the dish and started to differentiate were confirmed. The cell culture medium was replaced with 20 mL of fresh medium A.

Day 5: (a Half of the Medium was Replaced)

A half of the cell culture medium was replaced with 10 mL of fresh medium A.

Day 9: (a Half of the Medium was Replaced)

A half of the cell culture medium was replaced with 10 mL of fresh medium A.

Day 13: (Induced Mesodermal Cells were Transferred from OP9 Cell Layer onto OP9/DLL1 Cell Layer)

Cell culture medium was aspirated to remove and the surface of the cultured cells were washed with HBSS (+Mg+Ca) to washout the cell culture medium. 10 mL of Collagenase IV 250U in HBSS (+Mg+Ca) solution was added to the dish and incubated for 45 minutes at 37° C.

The collagenase solution was removed by aspiration and the cells were washed with 10 mL of PBS (−). Then, 0.05% trypsin/EDTA solution was added to the dish and the dish was incubated for 20 minutes at 37° C. After the incubation, the sheet like cell aggregates peeled from the bottom of the dish and the cell aggregates were mechanically fragmented to smaller sizes by means of pipetting. Thus treated cells were added with fresh medium A 20 mL and cultured for more 45 minutes at 37° C. The culture medium containing the floating cells was passed through 100 μm mesh and the cells were collected. The cells were then centrifuged at 1200 rpm for 7 minutes at 4° C. The obtained pellet was suspended in 10 mL of medium B. One-tenth of the suspension was separated and used for the FACS analysis. The remaining cell suspension was seeded on new dishes containing OP9/DLL1 cells. Cell suspensions obtained from several dishes were pooled and the pooled cells were seeded on the same number of new dishes.

Figure 16:
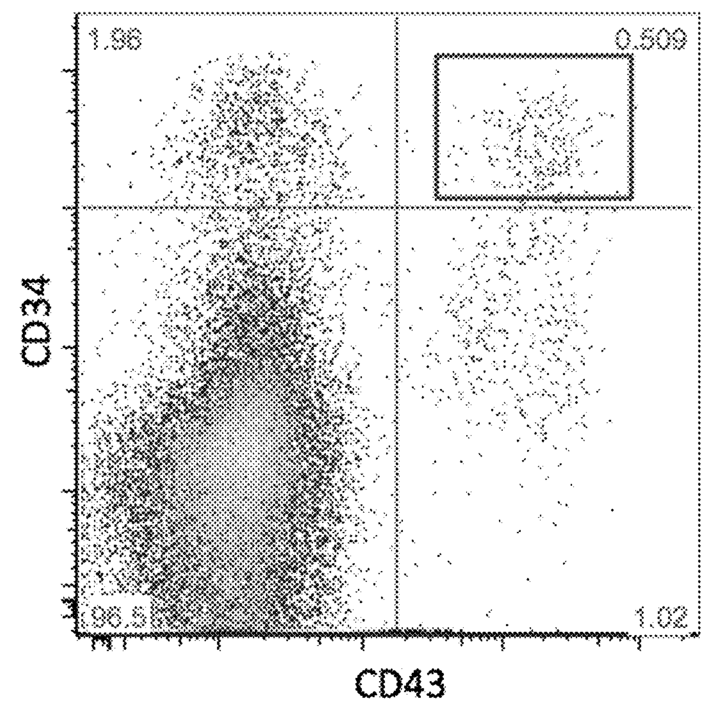
FIG. 16 is a result of FACS analysis of the cells on day 13 of the differentiation of T-iPS cells established from WT1 peptide specific T cells into T cells.

In order to ascertain whether or not hematopoietic progenitor cells were contained in the obtained cells, FACS analysis was carried out using anti-CD34 antibody, anti-CD43 antibody. The results are shown in FIG. 16. Since a sufficient number of cells could be confirmed in the $CD34^{low}CD43^{+}$ cell fraction, it was confirmed that hematopoietic progenitor cells were induced.

C. Induction of T Cells from Hematopoietic Progenitor Cells.

Then, the obtained cells were seeded on OP9/DLL1 cells. In this step, cell sorting of the $CD34^{low}CD43^{+}$ cell fraction was not performed. When this fraction is sorted, the efficiency of differentiation of T cells could be reduced in comparison with the case where sorting is not performed due to the decrease of the cells or damage to the cells by sorting.

Day 16: (Cells were Subcultured)

The cells loosely adhered to the OP9 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B. Thus prepared cells were seeded on new dishes containing OP9/DLL1 cells.

Day 23: (Cells were Subcultured) Blood Cell Colonies began to appear.

The cells loosely adhered to the OP9/DLL1 cells were gently dissociated by pipetting several times. The cells were passed through a 100 μm mesh and collected in a 50 mL conical tube. The tube was centrifuged at 1200 rpm for 7 minutes at 4° C. The pellet was dispersed in 10 mL of medium B.

Day 36: WT1 Tetramer Positive T Cells were Confirmed

Figure 17:
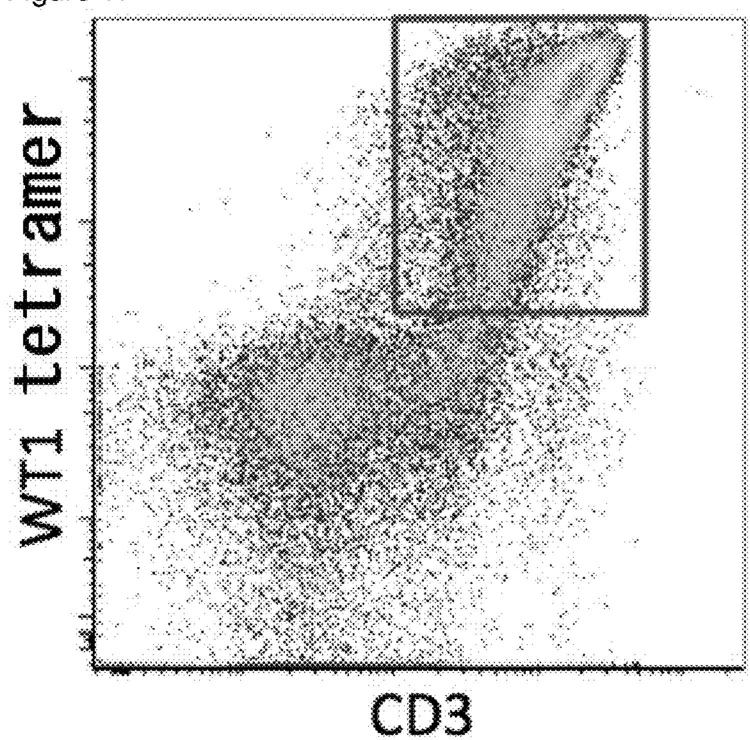
FIG. 17 is a result of FACS analysis of the cells on day 36 of the differentiation of T-iPS cells established from WT1 peptide specific T cells into T cells.

In order to confirm T cells specific for WT1 antigen were induced, the cells on Day 36 were analyzed by FACS with anti CD3 antibody and WT1 tetramer. Results are shown in FIG. 17. $CD3^{+}$ cells were observed and a most part of the cells were differentiated into $CD3^{+}$WT1 tetramer positive cells.

As shown above, the T cells re-generated from the T-iPS cells were confirmed to exhibit the same antigen specificity as the original T cells. Further, thus re-generated T cells expressed the surface antigen that were observed in mature T cells and therefore, had the well matured functions.

EXAMPLE 6

Preparation of iPS cells from HLA homozygous donor's monocyte introduced with WT1 antigen specific TCR iPS cell clone established from a monocyte of a donor with a homozygous HLA haplotype in Center for iPS cell Research and Application, Kyoto University were used.

Genes encoding TCR specific for HLA-A2402-restricted WT1 were cloned from a WT1 specific CTL clone "TAK1" established in Department of hematology, Ehime University. Genes encoding WT1-TCR were Vα20/J33/Cα and Vβ5.1/J2.1/Cβ2. TCRβ(Vβ5.1/J2.1/Cβ2)-p2A-TCRα (Vα20/J33/Cα) were inserted in this order into the Gateway System's entry vector to construct a plasmid.

1) Construction of WT1-TCR Lentiviral Vector

CS-UbC-RfA-IRES2-hKO1 vector gifted from Dr. Hiroyuki MIYOSHI of the Institute of Physical and Chemical Research, Japan was used. The Gateway System's Entry vector incorporated with the WT1-TCR genes and CS-UbC-RfA-IRES2-hKO1 vector were subjected to the LR clonase reaction (Life Technologies) to give a CS-UbC-RfA-IRES2-hKO1/WT1-TCR plasmid vector.

2) Preparation of Culture Supernatant Comprising WT1-TCR Lentiviral Vector

The above obtained CS-UbC-RfA-IRES2-hKO1/WT1-TCR was introduced into the packaging cell line LentiX-293T and the cells were cultured. The culture supernatant containing the WT1-TCR lentiviral vector was collected and the virus was condensed by ultra-centrifugation.

3) Establishment of an iPS Cell Clone from the WT1-TCR Transduced HLA Homozygous Monocyte.

iPS cells established from a monocyte with a homozygous HLA haplotypes and cultured on iMatrix (Nippi) were infected with the supernatant containing CS-UbC-RfA-IRES2-hKO1/WT1-TCR virus. The cells were observed under a fluorescence microscopy to confirm the expression of the hKO1 protein included in the vector, and confirmed that the WT1-TCR was duly introduced into the iPS cells to give WT1-TCR/mono-iPS cells.

4) Cloning of WT1-TCR/Mono-iPS Cells

Four days after the infection, the infected iPS cells were removed from the dish and sorted the hKO1 expressing cells by using FACS Aria without staining the cells to give WT1-TCR/mono-iPS balk. The hKO1 positive cells were seeded on the iMatrix and cultured for one week. After one week culture, the expanded colonies were observed under the fluorescence microscopy and colonies strongly expressing hKO1 were mechanically picked up and cloned to give WT1-TCR/mono-iPS clones. The cells sorted based on the expression of hKO1 and the cloned cells were both differentiated towards T cells in the similar manner as taught in WO2013176197A1.

Figure 18:
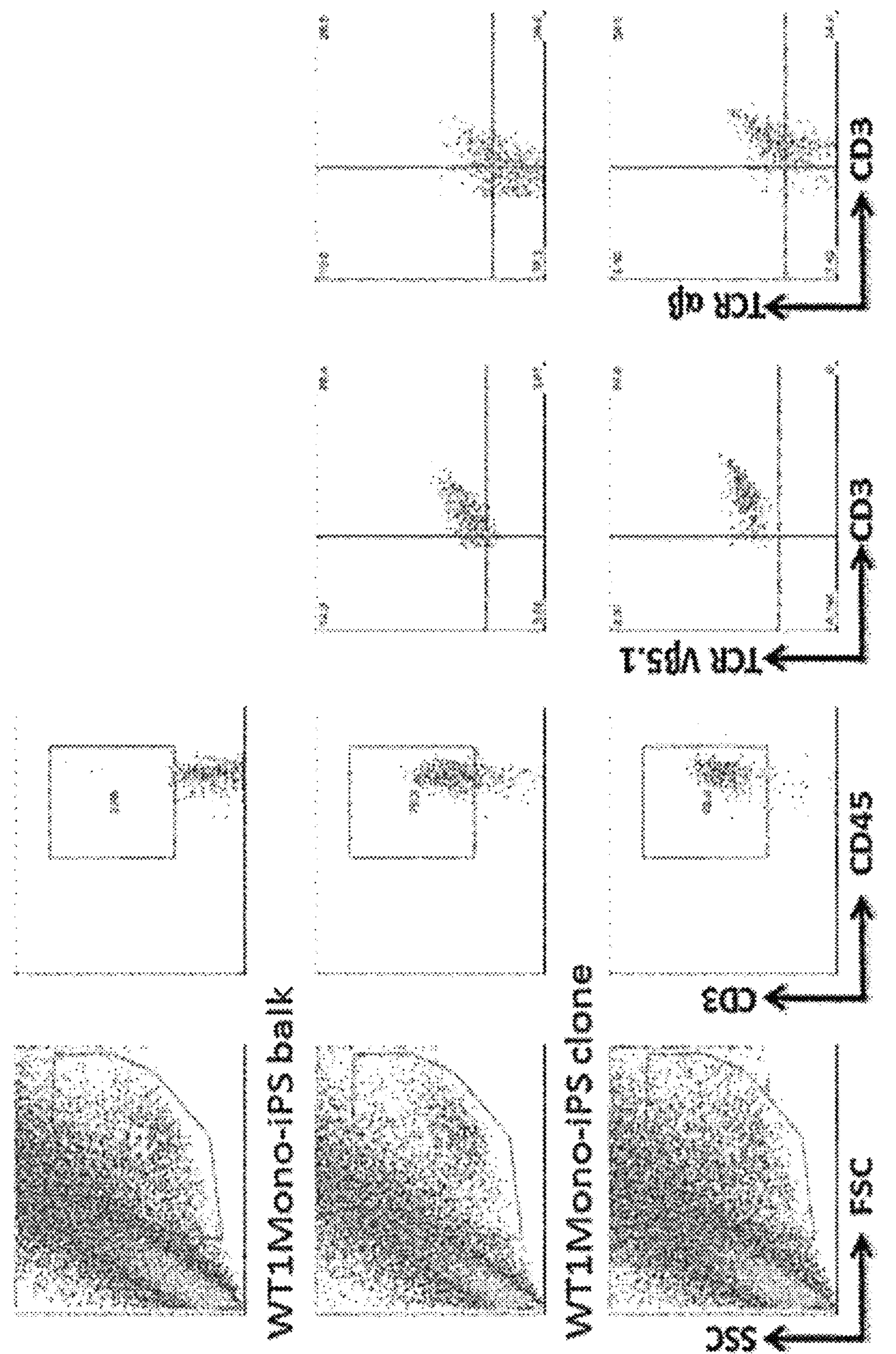
FIG. 18 is a result of FACS analysis of the T cells differentiated from TCR introduced iPS cells in Example 6.

In particular, small iPS cell mass (less than 100 cells) was transferred on previously irradiated C3H10T1/2 cells and cultured in the EB medium supplemented with 20 ng/mL of VEGF, 50 ng/mL of SCF and 50 ng/mL of FLT-3L (Peprotech). On day 14 of the culture, the hematopoietic cells contained in the iPS-sac structure were collected and transferred on the irradiated OP9-DL1 cells, and cultured in OP9 medium supplemented with 10 ng/mL of FLT-3 and 1 ng/mL of IL-7. FACS analysis of the cells on day 38 of the differentiation is shown in FIG. 18.

On day 38 of the differentiation, mono-iPS cells, WT1-TCR/mono-iPS balk, and WT TCR/mono-iPS cell clone were analyzed with FACS Aria. iPS cells derived from monocyte (mono-iPS cells) did not express CD3 while iPS cells introduced with WT1-TCR expressed CD3. Almost 100% of the CD3 positive cells were also positive for Vβ5.1 antibody. Vβ5.1 was included in the introduced TCR chain. The cells were also positive for TCRαβ antibody. It was confirmed that the introduced WT1-TCR were functionally expressed on the surface of the cells.

EXAMPLE 7 iPS cell clone TKT3v1-7 obtained by introducing the Yamanaka factors into a T cell was gifted from The University of Tokyo, Japan. The cells are abbreviated as "TKT3V".

1. gDNA targeting to human RAG2 gene having PAM sequence was designed and incorporated into an expression plasmid having H3 promoter. gDNA was designed to remove the underlined two bases in one allele of the target sequence of GGTTATGCTTTACATCCAGATGG (SEQ ID NO: 3) and to insert one base on the 5' side of the underlined part in the other allele.

2. The above prepared plasmid together with the Cas9 protein expressing plasmid were transfected into human peripheral blood-T cell derived iPS cells (TKT3V).

Figure 19:
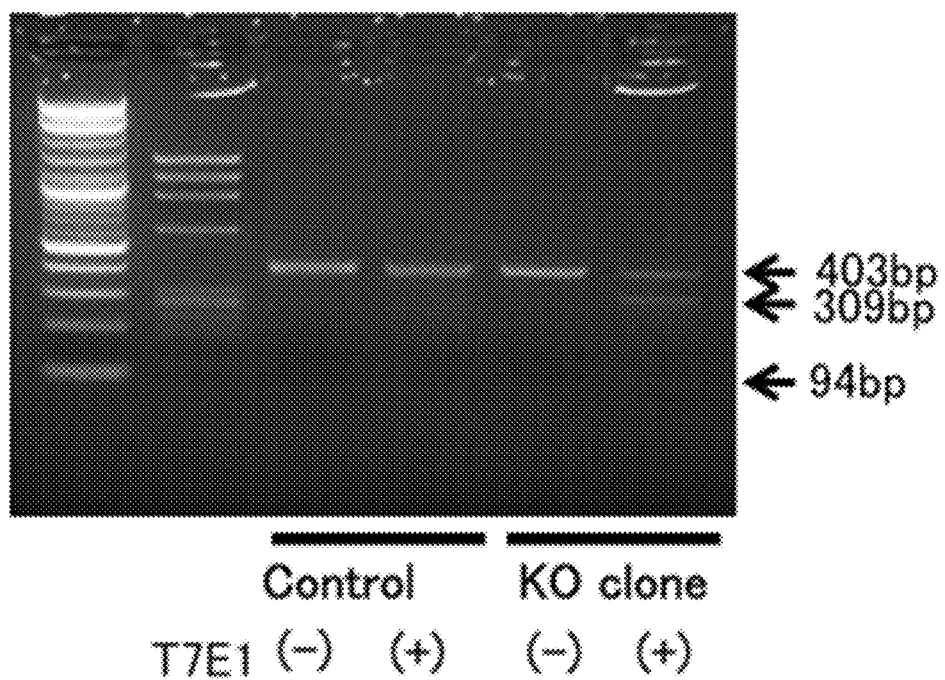
FIG. 19 shows the result of T7E assay on the genome of Rag2 gene knockout T-iPS cells in Example 7.

3. The transfected iPS cells were cloned and 50 clones were obtained. The 50 clones were screened for mismatch on the genome by the T7E1 assay (FIG. 19).

4. The screened clones were subjected to sequencing of the RAG2 gene and a clone containing a missense mutation in said gene of both alleles was selected(TKT3V/RAG2KO).

5. The selected iPS clone was subjected to chromosomal analysis and assessment of pluripotency by teratoma formation. No abnormality was observed in the cells as genetically modified iPS cells.

Figure 20:
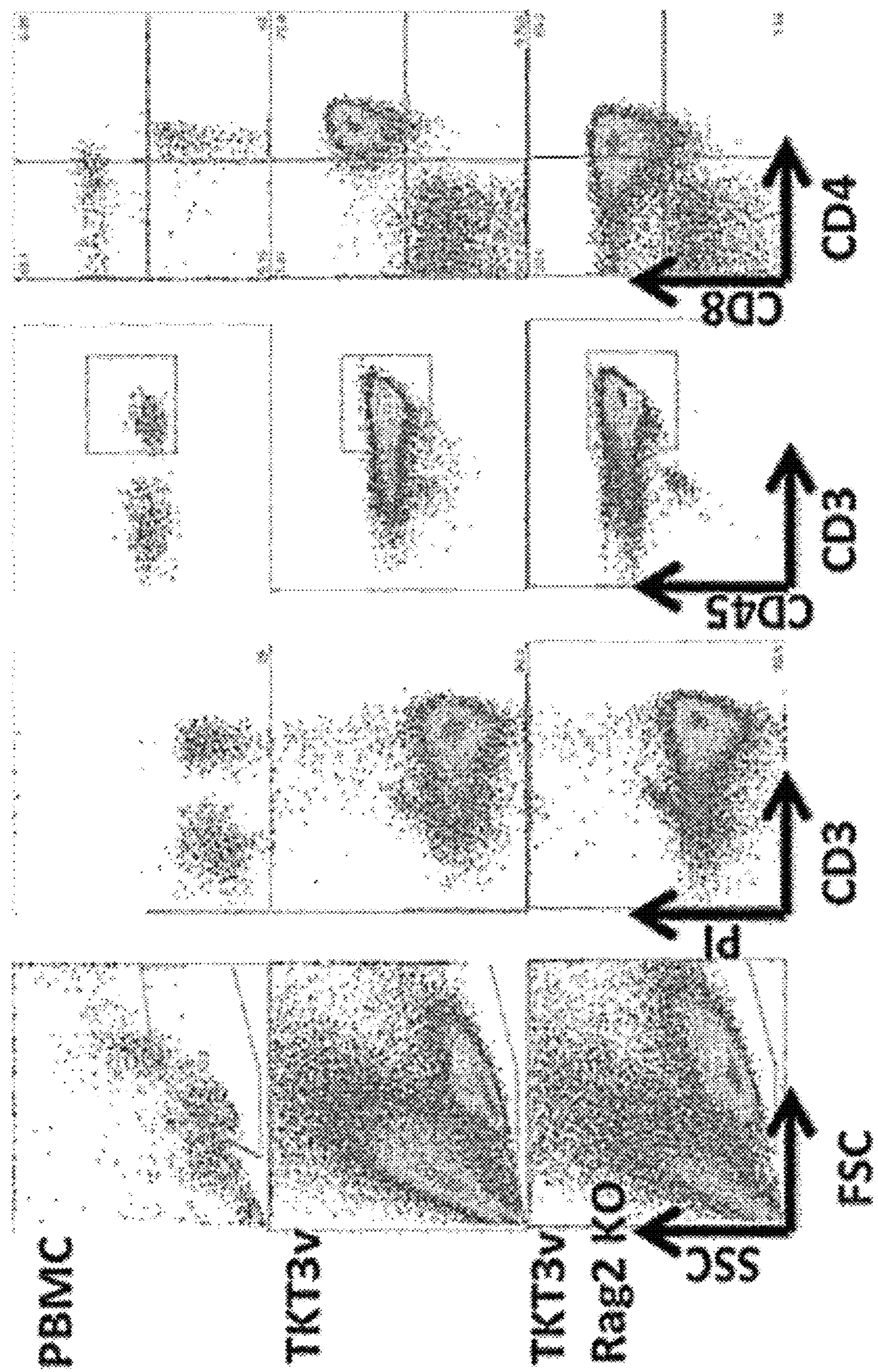
FIG. 20 shows the results of FACS analysis of T cells differentiated from T-iPS cells (TKT3v) and Rag2 knockout T-iPS cells (Rag2KO) in Example 7.

6. The iPS cell clones of TKT3V and TKT3V/RAG2KO were differentiated into T cells in the same manner as taught in WO2013176197A1. In particular, small iPS cell mass (less than 100 cells) was transferred on irradiated C3H10T1/2 cells and cultured in EB medium supplemented with 20 ng/mL of VEGF, 50 ng/mL of SCF, and 50 ng/mL of FLT-3L (Peprotech). On day 14 of the culture, the hematopoietic cells contained in the iPS-sac structure were collected and transferred on the irradiated OP9-DL1 cells and cultured in OP9 medium supplemented with 10 ng/mL of FLT-3 and 1 ng/mL of IL-7. FACS analysis of the induced cells is shown in FIG. 20. Generation of $CD4^{+}CD8^{+}$ DP cell population was observed.

7. The DP cell population was isolated by flow cytometry and mRNA was extracted from the cells.

Figure 21:
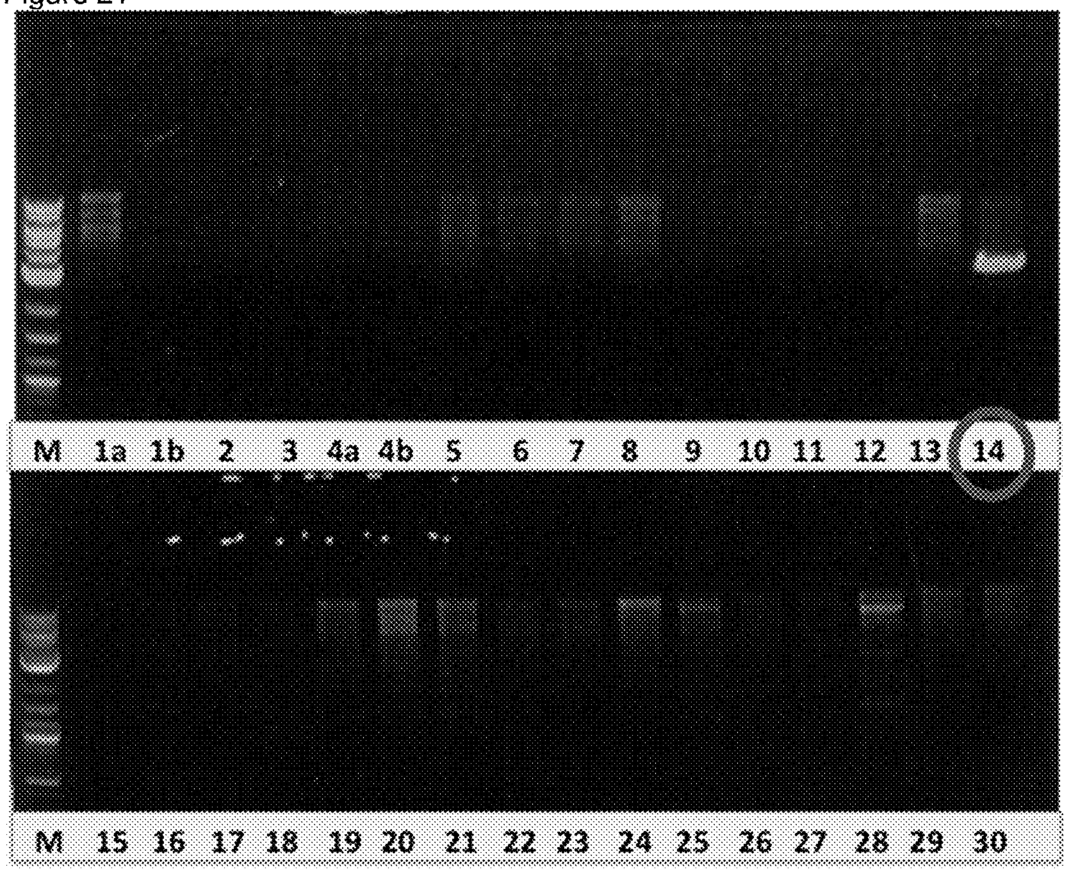
FIG. 21 shows the results of RT-PCR on T-iPS cells (TKT3v) with primers targeting each segment in the V and C regions in the TCRα chain of TKT3v.

8. RT-PCR was conducted on the extracted mRNA with primers targeting each segment in the V and C regions of the TCRα chain and detected the rearrangement of the TCRα chain. RT-PCR was also conducted on the mRNA of TKT3V in the same manner. The TKT3V cells had only Va14 as TCRα chain (FIG. 21).

Figure 22:
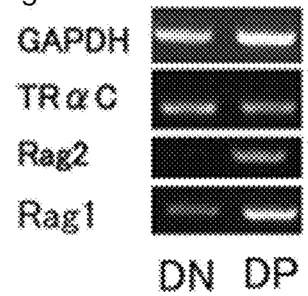
FIG. 22 shows that the Rag2 in the T-iPS cells (TKT3v) was activated upon differentiation of the cells from CD4CD8 double negative cells into CD4CD8 double positive T cells.
Figure 23:
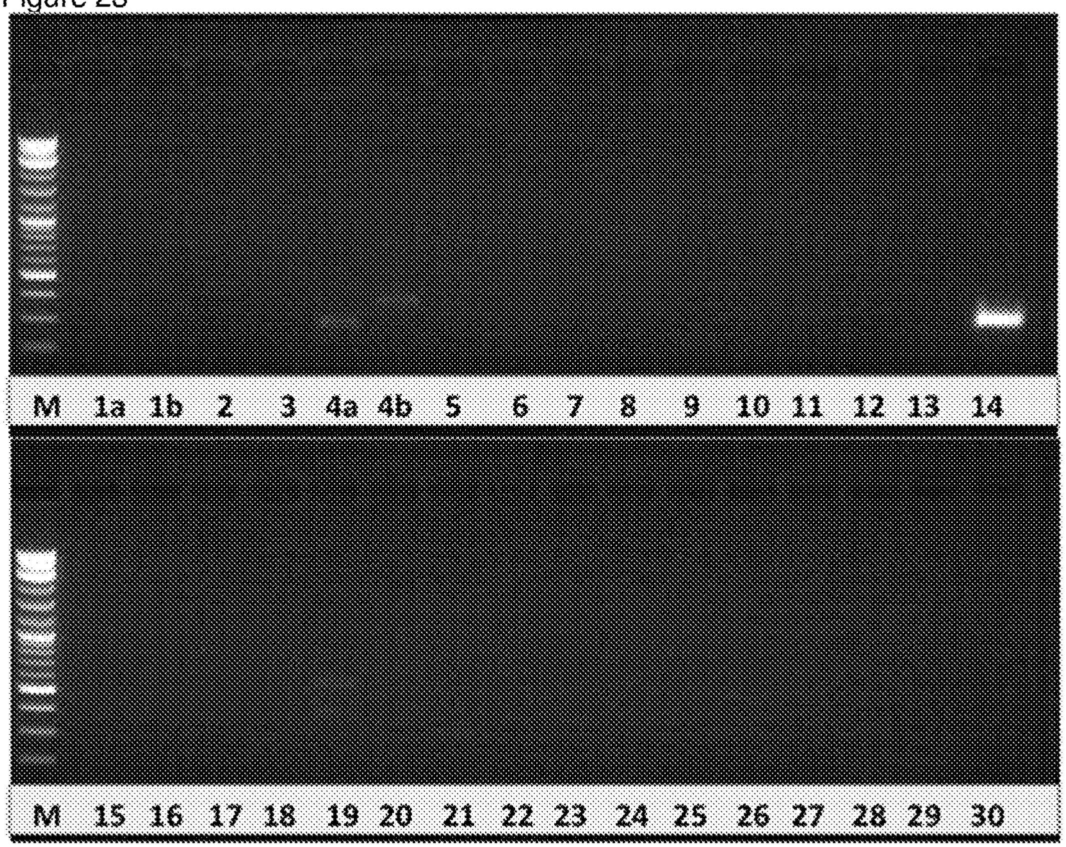
FIG. 23 shows the results of RT-PCR on CD4CD8 double negative T cells differentiated from T-iPS cells (TKT3v) with primers targeting each segment in the V and C regions in the TCRα chain of TKT3v.
Figure 24:
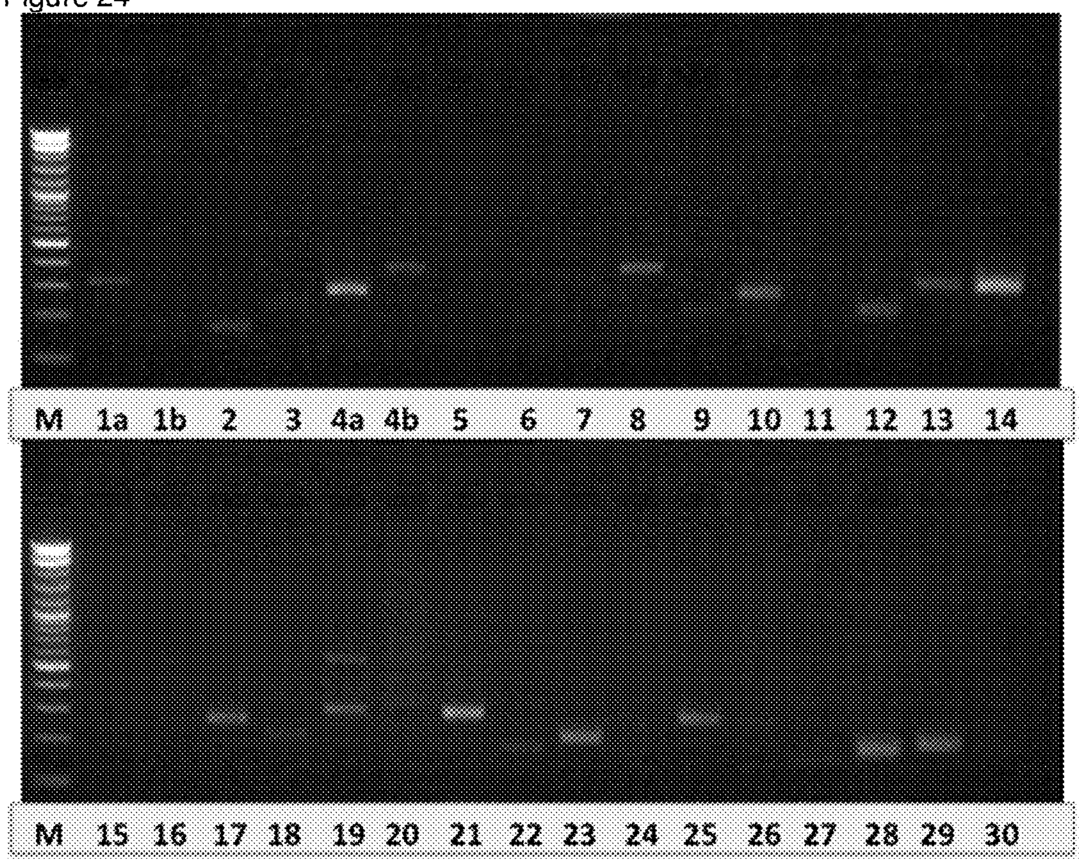
FIG. 24 shows the results of RT-PCR on CD4CD8 double positive T cells differentiated from T-iPS cells (TKT3v) with primers targeting each segment in the V and C regions in the TCRα chain of TKT3v.

During the differentiation of TKT3V cells (iPS cells) into T cells, RAG2 reactivation was confirmed in the cells differentiated from $CD4^{-}CD8^{-}$ double negative (DN) cells into double positive (DP) cells (FIG. 22). The rearrangement of the TCRα chains in the DN and DP stages of the T cells are shown in FIG. 23 and FIG. 24, respectively. In the DN cells, similar to the iPS cells, only Va14 rearrangement was confirmed. In the DP cells, rearrangements of segments other than Va14 were frequently observed. It seems that the activation of the RAG protein caused rearrangement of the TCRα chain. This nonspecific rearrangement may result in loss of the antigen specificity of the induced T cells.

Figure 25:
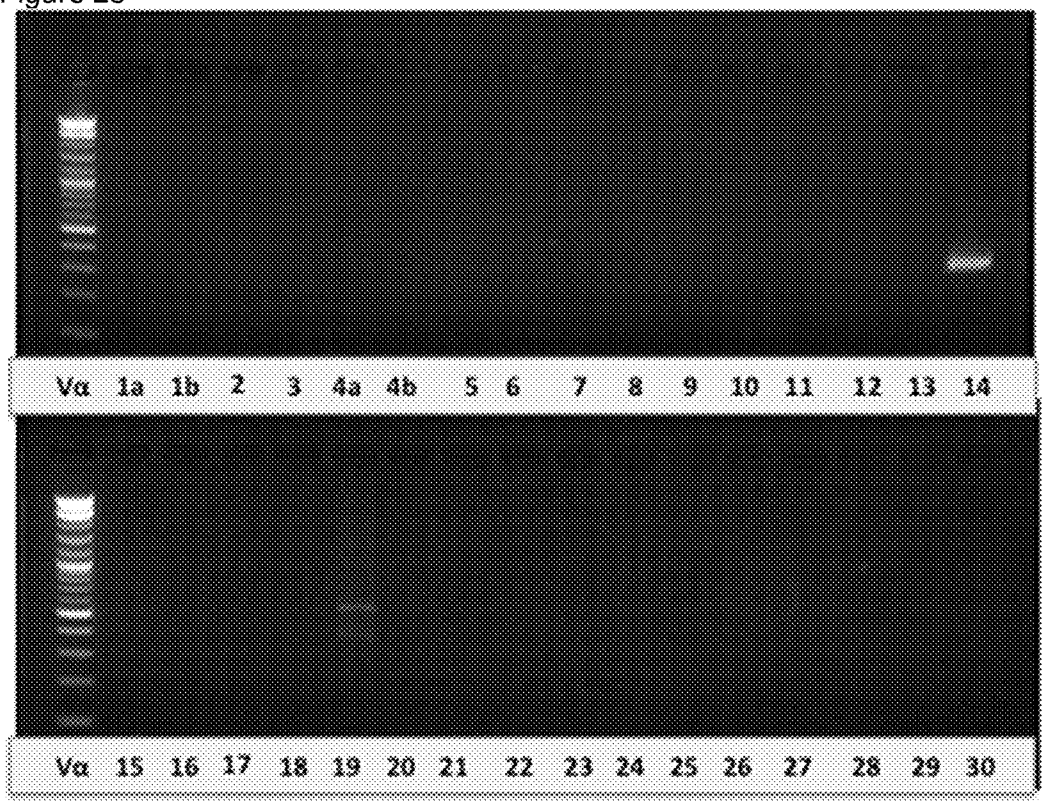
FIG. 25 shows the TCRα chain rearrangement in the DP cells differentiated from Rag2 knockout TKT3v/Rag2KO iPS cells.

The TCRα chain rearrangement of DP cells differentiated from TKT3v/RAG2KO clone, i.e. RAG2 knockout iPS cells is shown in FIG. 25. In the DP cells differentiated from the RAG2 knockout clone, no rearrangement of the genes other than Va14 was observed. It is considered that Rag2 gene knockout failed to produce RAG2 protein and prevented rearrangement of the TCRα chain.

It was confirmed to be possible to prevent additional rearrangement of TCRα chain and to retain the antigen specificity in the T cells differentiated from iPS cells by introducing a missense mutation into the RAG2 gene at the stage of iPS cells.

Figure 26:
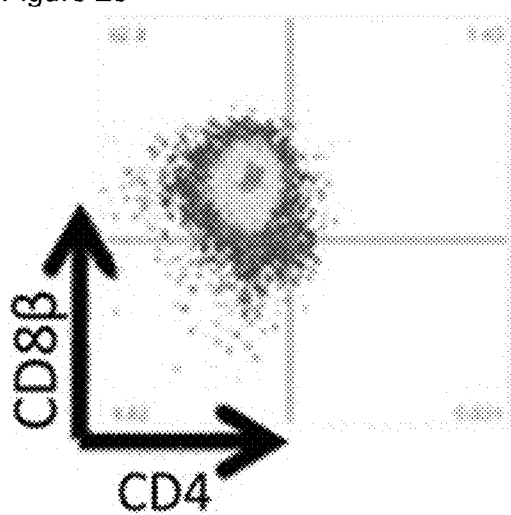
FIG. 26 shows that CD8 single positive mature T cells were differentiated from CD4CD8 double positive cells induced from TKT3V/RAG2KO iPS cells.
Figure 27:
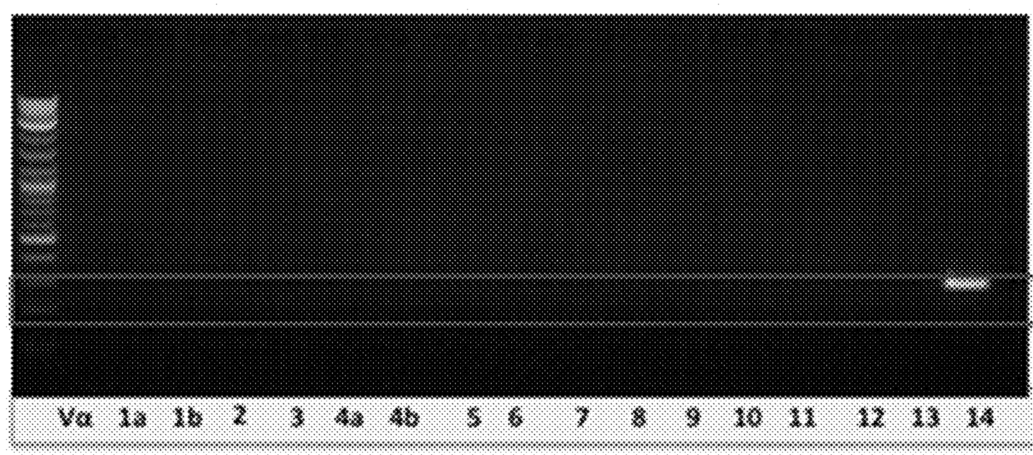
FIG. 27 shows that the TCR chain rearrangement in the CD8 single positive T cells differentiated from Rag2 knockout TKT3v/Rag2KO iPS cells was confirmed.
Figure 27:
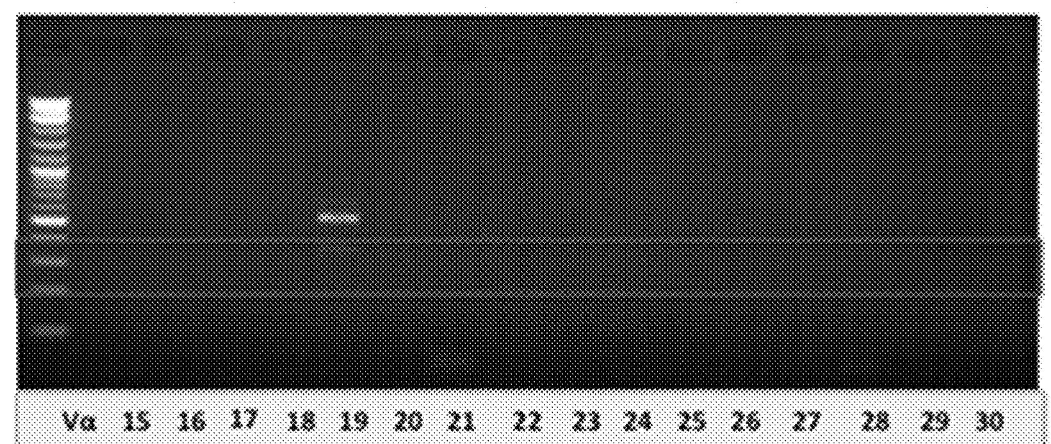

The DP cells differentiated from the TKT3V/RAG2KO clone were further differentiated by the conventional procedure into CD8 single positive cytotoxic T lymphocytes (FIG. 26). CD8 single positive cell population was isolated by using a flow cytometry and mRNA of the isolated cells was extracted. The TCR rearrangement was examined by RT-PCR. Results are shown in FIG. 27. The CD8 single positive T cells differentiated from the gene modified iPS cells held only Va14 as the rearranged gene. The band in the Va19 lane is a nonspecific band out of the size of TCRa enclosed by the frame in this figure.

EXAMPLE 8

Knockout of Rag2 gene in the iPS cells established from a human monocyte with a homozygous HLA haplotype 1. An iPS cell clone established from a human monocyte was used. The iPS cell clone was established from a peripheral blood monocyte of a donor homozygous for the HLA haplotype of HLA-A*3303-B*4403-C*1403-DRB1*1302. The iPS cells used here were those maintained under a feeder free condition according to the protocol CiRA_FFiPSC_protocol_JP_v140310 provided by Center for iPS cell Research and Application, Kyoto University, Japan.

2. Double cleavages were made in the exon 1 of human Rag2 gene in the iPS cells. Specifically, between positions 440 to 441 and 679 to 680 of the exon 1 nucleotide were cleaved by CRISPR-Cas9.

3. The target sgRNAs were as follows:

```
i)
sense chain:
                              (SEQ ID NO: 4)
caccGATTAATGTGGTGTACAGCCG
```

-continued

```
anti-sense chain:
                                    (SEQ ID NO: 5)
aaacCGGCTGTACACCACATTAATC

ii)
sense chain:
                                    (SEQ ID NO: 6)
caccGTTGGCAGGCCGGATATTAT

anti-sense chain:
                                    (SEQ ID NO: 7)
aaacATAATATCCGGCCTGCCAAC
```

4. The above sgRNA was inserted into plasmid pSpCas9 (BB)-2A-Puro (PX459) purchased from addgene. The iPS cells were enzymatically treated to give single cell suspension and transfected with the plasmid by means of electroporation with NEPA21 (Nepagene).

5. After the transfection, the cells were seeded in a plate and cultured in the presence of puromycin and then, plural clones were picked up.

DNA was collected from each clone and the presence or absence of deletion of the gene was examined by PCR. Primers used for PCR were as follows.

```
For:
                                    (SEQ ID NO: 8)
CCCAAAAGATCCTGCCCCACTGG

Rev:
                                    (SEQ ID NO: 9)
AGTCAGGATTGCACTGGAGACAG
```

7. 57 clones in total were picked up and evaluated as follows based on the results of the PCR.

i) Clones without deletion: 31 ii) Clones in which deletion was occurred in a single allele: 14 iii) Clones in which deletions were occurred in both alleles: 2

Figure 28:
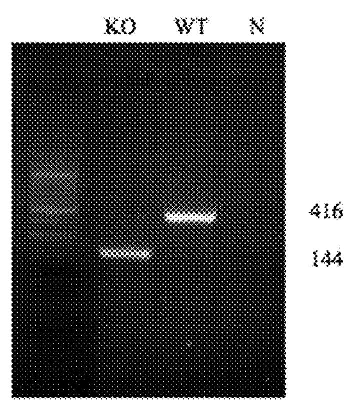
FIG. 28 shows that Rag2 gene was knocked out in Example 8.

8. PCR analysis of the original iPS cell clone (WT) and iPS cell clone in which deletions were occurred in both alleles (RAG2KO) are shown in FIG. 28. The shortened band represents that deletions were occurred in both alleles.

9. Two RAG2 knockout iPS cell clones were established.

EXAMPLE 9

Figure 29:
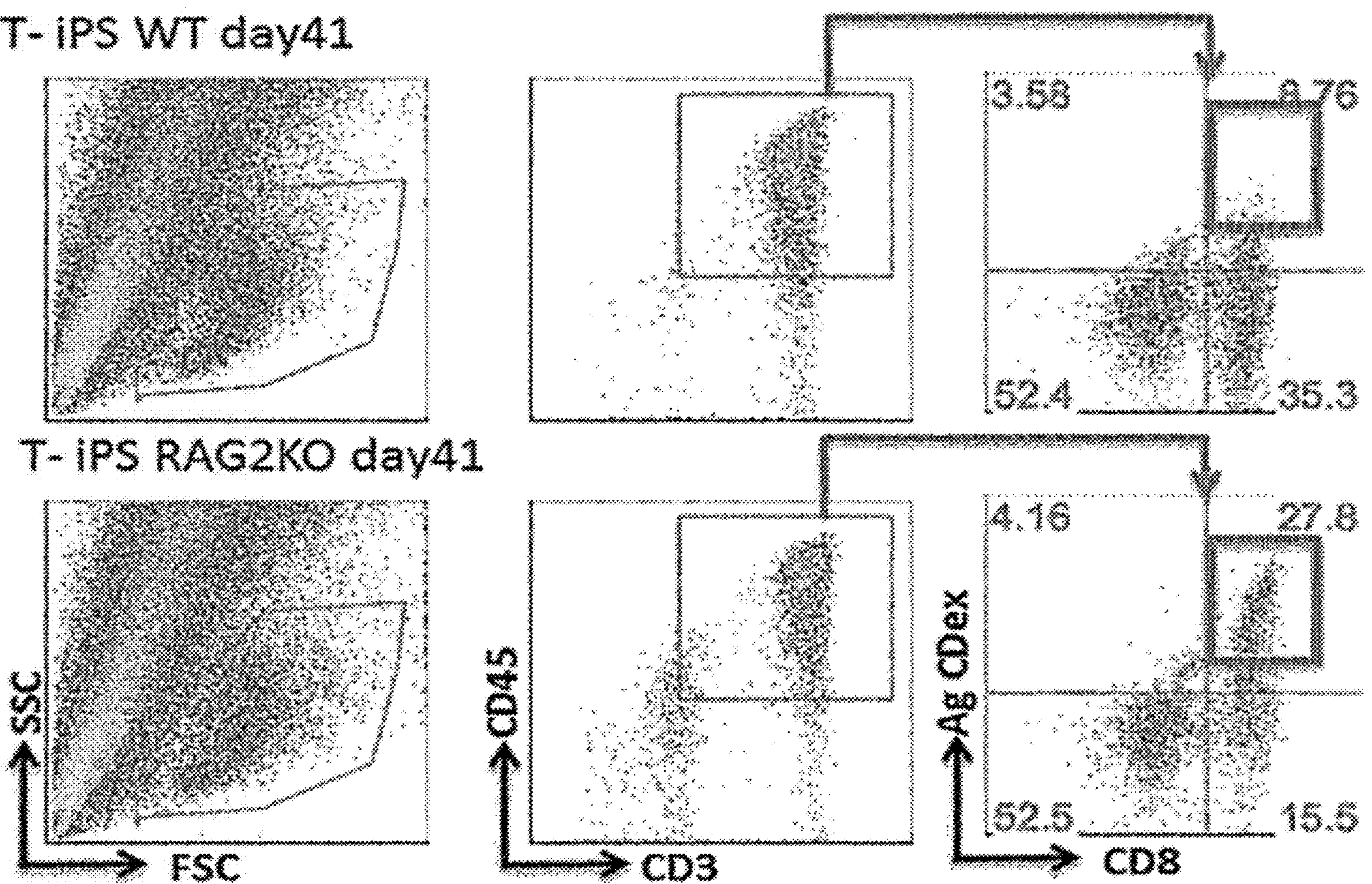
FIG. 29 shows results of FACS analysis of T cells differentiated over a relatively long period of time from T-iPS cells (WT) and Rag2 knockout T-iPS cells (Rag2KO) in Example 9.
Figure 30:
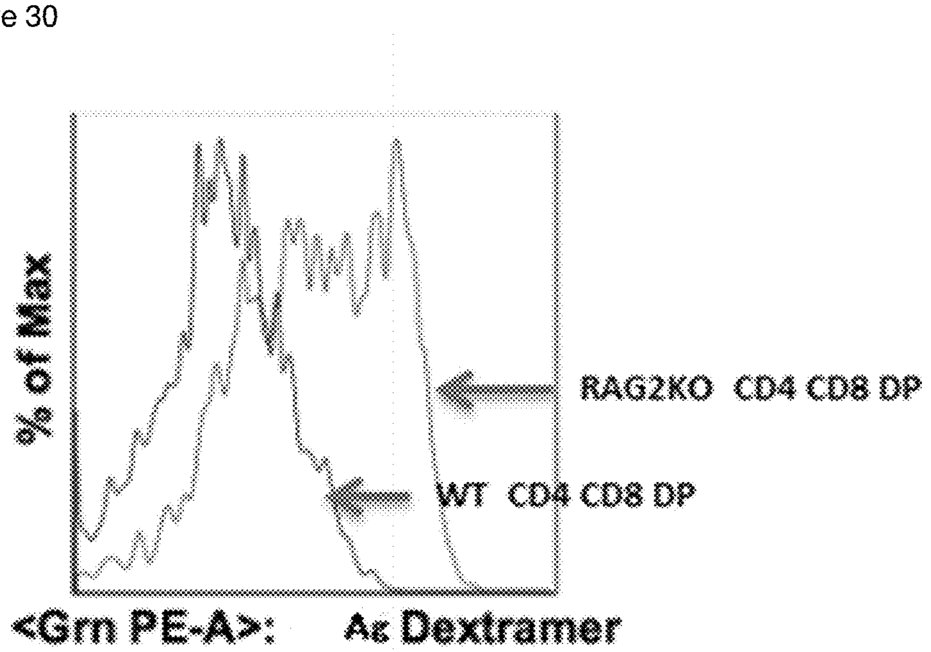
FIG. 30 shows that CD8 positive cells differentiated from Rag2 knockout T-iPS cells maintained the TCR in Example 9.

T-iPS cells established by introducing the Yamanaka factors into an antigen specific CD8 single positive T cell, other than those used in Example 7, were used. Rag2 gene in the T-iPS cells was knocked out in the same manner as Example 7. The T-iPS cells without Rag2 knockout (WT) and Rag2 knockout T-iPS cells were differentiated into T cells in the same manner as Example 7. On day 41 of the culture in the OP9 medium (on day 55 of the differentiation), the cells were analyzed. Results are shown in FIGS. 29 and 30. In the figures, AgDex represents the multimer (Dextramer) of the antigen to which the T cell from which the T-iPS cells were established bound specifically.

T cells differentiated from the Rag2 knockout iPS clone over a relatively long period of time maintained relatively strong affinity to the tetramer (more than 60% of the CD8 positive cells). On the other hand, many of the T cells differentiated from WT clone did not maintain the TCR specificity.

What is claimed is:

1. An in vitro method for inducing T cells for a cell-based immunotherapy, where the T cells are CD8 single positive T cells derived from human pluripotent stem cells, comprising the steps of:

(i) providing human pluripotent stem cells having both alleles of Rag-1 or Rag-2 gene knocked out and comprising genes encoding an alpha chain and a beta chain of a T cell receptor specific for a desired antigen, wherein the human pluripotent stem cells of step (i) are prepared by a method comprising the steps of:

(a) introducing genes encoding the alpha chain and beta chain of the antigen specific T cell receptor for the desired antigen into the pluripotent stem cells; and (b) knocking out both alleles of the Rag-1 or Rag-2 gene in the human pluripotent stem cells provided in step (a) by genome editing;

(ii) inducing the pluripotent stem cells of step (i) into a population of CD3 positive T cells, wherein the population of CD3 positive T cells comprise CD4CD8 double positive T cells, and CD4CD8 double negative T cells;

(iii) isolating only the CD4CD8 double positive T cells from the population of T cells in step (ii) using flow cytometry; and (iv) inducing CD8 single positive T cells, which are differentiated from the isolated CD4CD8 double positive T cells of step (iii), and wherein the CD8 single positive T cells have no rearrangement of the alpha chain of the T cell receptor specific for the desired antigen.

2. The method according to claim 1, wherein the human pluripotent stem cells are human iPS cells.

3. The method according to claim 1, wherein the Rag-1 or Rag-2 gene is knocked out by CRISPR-Cas9.

4. The method of claim 2, wherein the iPS cells have a homozygous HLA haplotype that matches at least one of HLA haplotypes of a subject to be treated.

* * * * *

SEQUENCE LISTING

```
<160> NUMBER OF SEQ ID NOS: 9

<210> SEQ ID NO 1
<211> LENGTH: 9
<212> TYPE: PRT
<213> ORGANISM: Homo sapiens

<400> SEQUENCE: 1

Ile Tyr Val Leu Val Met Leu Val Leu
1               5


<210> SEQ ID NO 2
<211> LENGTH: 9
<212> TYPE: PRT
<213> ORGANISM: Homo sapiens

<400> SEQUENCE: 2

Cys Tyr Thr Trp Asn Gln Met Asn Leu
1               5


<210> SEQ ID NO 3
<211> LENGTH: 23
<212> TYPE: DNA
<213> ORGANISM: Homo sapiens

<400> SEQUENCE: 3

ggttatgctt tacatccaga tgg                                    23


<210> SEQ ID NO 4
<211> LENGTH: 25
<212> TYPE: DNA
```

```
<213> ORGANISM: Homo sapiens

<400> SEQUENCE: 4

caccgattaa tgtggtgtac agccg                                            25


<210> SEQ ID NO 5
<211> LENGTH: 25
<212> TYPE: DNA
<213> ORGANISM: Homo sapiens

<400> SEQUENCE: 5

aaaccggctg tacaccacat taatc                                            25


<210> SEQ ID NO 6
<211> LENGTH: 24
<212> TYPE: DNA
<213> ORGANISM: Homo sapiens

<400> SEQUENCE: 6

caccgttggc aggccggata ttat                                             24


<210> SEQ ID NO 7
<211> LENGTH: 24
<212> TYPE: DNA
<213> ORGANISM: Homo sapiens

<400> SEQUENCE: 7

aaacataata tccggcctgc caac                                             24


<210> SEQ ID NO 8
<211> LENGTH: 23
<212> TYPE: DNA
<213> ORGANISM: Homo sapiens

<400> SEQUENCE: 8

cccaaaagat cctgccccac tgg                                              23


<210> SEQ ID NO 9
<211> LENGTH: 23
<212> TYPE: DNA
<213> ORGANISM: Homo sapiens

<400> SEQUENCE: 9

agtcaggatt gcactggaga cag                                              23
```